US010856564B2

(12) United States Patent
Moreno Egea et al.

(10) Patent No.: US 10,856,564 B2
(45) Date of Patent: Dec. 8, 2020

(54) PROCESS FOR THE PREPARATION AND STABILIZATION OF EMULSIONS WITH OMEGA-3 BY MEANS OF ISOMETRIC CRYSTALLINE NETWORKS OF CELLULOSE DERIVATIVES

(71) Applicant: SOLUTEX NA, LCC, Miami, FL (US)

(72) Inventors: Fernando Moreno Egea, Alcobendas Madrid (ES); Antonio Martínez Férez, Granada (ES)

(73) Assignee: Solutex NA, LCC, Miami, FL (US)

( * ) Notice: Subject to any disclaimer, the term of this patent is extended or adjusted under 35 U.S.C. 154(b) by 0 days.

(21) Appl. No.: 15/763,763

(22) PCT Filed: Oct. 3, 2016

(86) PCT No.: PCT/IB2016/055902
§ 371 (c)(1),
(2) Date: Mar. 27, 2018

(87) PCT Pub. No.: WO2017/056075
PCT Pub. Date: Apr. 6, 2017

(65) Prior Publication Data
US 2018/0271131 A1 Sep. 27, 2018

(30) Foreign Application Priority Data
Oct. 1, 2015 (ES) .................................. 201531406

(51) Int. Cl.
| A23L 29/10 | (2016.01) |
| A61K 9/107 | (2006.01) |
| A23L 29/262 | (2016.01) |
| A23L 33/115 | (2016.01) |
| A61K 47/12 | (2006.01) |
| A61K 47/38 | (2006.01) |
| A61P 29/00 | (2006.01) |

(52) U.S. Cl.
CPC ............ *A23L 29/10* (2016.08); *A23L 29/262* (2016.08); *A23L 33/115* (2016.08); *A61K 9/107* (2013.01); *A61K 47/12* (2013.01); *A61K 47/38* (2013.01); *A23V 2002/00* (2013.01); *A23V 2250/187* (2013.01); *A23V 2250/1868* (2013.01); *A23V 2250/192* (2013.01); *A23V 2250/5086* (2013.01); *A23V 2250/51082* (2013.01); *A23V 2250/51084* (2013.01); *A61P 29/00* (2018.01)

(58) Field of Classification Search
CPC ........ A61P 29/00; A23L 29/10; A23L 29/262; A23L 33/115; A23V 2250/1868; A23V 2250/187; A61K 47/38; A61K 9/107; A61K 31/557

See application file for complete search history.

(56) References Cited

U.S. PATENT DOCUMENTS

| 2,463,738 | A | 3/1949 | Bernhart |
| 3,089,823 | A | 5/1963 | Czarnecki |
| 5,773,073 | A | 6/1998 | Matsuda et al. |
| 6,007,856 | A | 12/1999 | Cox et al. |
| 8,512,687 | B2 | 8/2013 | Lambert et al. |
| 2004/0116408 | A1* | 6/2004 | Serhan ..................... C07C 59/42 514/218 |
| 2006/0029622 | A1 | 2/2006 | Floter et al. |
| 2006/0251685 | A1* | 11/2006 | Yu .......................... A61K 9/0048 424/400 |
| 2007/0259957 | A1* | 11/2007 | Ueshima .................. A61K 9/06 514/546 |
| 2009/0142324 | A1 | 6/2009 | Ikehara et al. |
| 2009/0208472 | A1 | 8/2009 | Sakai et al. |
| 2012/0251685 | A1* | 10/2012 | Wang-Nolan ........ A23D 7/0053 426/250 |
| 2013/0004617 | A1* | 1/2013 | Zhang ..................... B01J 13/10 426/72 |
| 2014/0170247 | A1 | 6/2014 | Hendler |
| 2015/0238424 | A1 | 8/2015 | Hiramura et al. |

FOREIGN PATENT DOCUMENTS

| CA | 2455226 C | 9/2002 |
| CA | 2008/000301 | 8/2008 |
| CA | 2008/000530 | 9/2008 |
| CN | 100486567 C | 2/2006 |
| CN | 103432588 A | 12/2013 |
| CN | 104274836 A | 1/2015 |
| CN | 104366508 A | 2/2015 |
| EP | 1116515 A2 | 7/2001 |
| EP | 0868918 B1 | 4/2004 |
| EP | 2595611 A2 | 5/2013 |

(Continued)

OTHER PUBLICATIONS

International Search Report dated Dec. 20, 2016, for PCT application No. ES2016/055902.
Written Opinion of the International Searching Authority dated Dec. 20, 2016, for PCT application No. ES2016/055902.
Ardalan, et al., "Antioxidant supplementation in hypertension", Journal of Renal Injury Prevention, vol. 3, Nov. 3, 2013, pp. 39-40.
Baradaran, "Lipoprotein(a), type 2 diabetes and nephropathy; the mystery continues", Journal of Nephropathology, vol. 1, Oct. 1, 2012, pp. 126-129.

(Continued)

*Primary Examiner* — Mark V Stevens
(74) *Attorney, Agent, or Firm* — Womble Bond Dickinson (US) LLP

(57) ABSTRACT

The present invention relates to a novel emulsion structured in an isometric crystalline network of cellulose derivatives where the emulsion comprises Omega-3 fatty acids homogeneously distributed in the same. The emulsion of the invention has been designed to have greater stability, bioavailability and gastro-resistance and may be used in special medical foods, nutritional supplements, sports nutrition, enteral nutrition or child nutrition, amongst others.

20 Claims, 2 Drawing Sheets

(56) References Cited

FOREIGN PATENT DOCUMENTS

| EP | 2344140 B1 | 8/2014 |
|---|---|---|
| EP | 2902101 A1 | 8/2015 |
| UA | 99889 C2 | 10/2012 |
| WO | WO 99/63841 A1 | 12/1999 |
| WO | WO 2003004015 A1 | 1/2003 |
| WO | WO2008/145183 A1 | 12/2008 |
| WO | WO 2011049629 A2 | 4/2011 |
| WO | WO 2014051116 A1 | 4/2014 |
| WO | WO2015102189 A1 | 7/2015 |
| WO | WO2015104440 A1 | 7/2015 |

OTHER PUBLICATIONS

Birch, et al., "Retinal Development in Very-Low-Birth-Weight Infants Fed Diets Differing in Omega-3 Fatty Acids", Investigative Ophthalmology & Visual Science, vol. 33, Jul. 1992, pp. 2365-2376.

Birch, et al., "Dietary Essential Fatty Acid Supply and Visual Acuity Development", Investigative Ophthalmology & Visual Science, vol. 33, Oct. 1992, pp. 3242-3253.

Bourre, et al., "The Effects of Dietary a-Linolenic Acid on the Composition of Nerve Membranes, Enzymatic Activity, Amplitude of Electrophysiological Parameters, Resistance to Poisons and Performance of Learning Tasks in Rats", The Journal of Nutrition, vol. 119, Dec. 1, 1989, pp. 1880-1892.

Cao, et al., "Docosahexaenoic acid promotes hippocampal neuronal development and synaptic function", Journal of Neurochemistry, vol. 111, Aug. 13, 2009, pp. 510-521.

Carlson, et al., "Visual-acuity development in healthy preterm infants: effect of marine-oil supplementation", American Journal of Clinical Nutrition, vol. 58, Jul. 1993, pp. 35-42.

Cheatham, et al., "n-3 Fatty acids and cognitive and visual acuity development: methodologic and conceptual considerations", American Journal of Clinical Nutrition, vol. 83, Jun. 2006, pp. 1458S-1466S.

Cruz-Hernandez, et al., "Benefits of Structured and Free Monoacylglycerols to Deliver Eicosapentaenoic (EPA) in a Model of Lipid Malabsorption", Nutrients, vol. 4, Nov. 21, 2012, pp. 1781-1793.

Dalli, et al., "Novel n-3 Immunoresolvents: Structures and Actions", Scientific Reports, vol. 3, Jun. 5, 2013.

Guesnet, et al., "Blood lipid concentrations of docosahexaenoic and arachidonic acids at birth determine their relative postnatal changes in term infants fed breast milk or formula", American Journal of Clinical Nutrition, vol. 70, Aug. 1999, pp. 292-298.

Dyall, "Long-chain omega-3 fatty acids and the brain: a review of the independent and shared effects of EPA, DPA and DHA", Frontiers in Aging Neuroscience, vol. 7, Apr. 21, 2015.

Garaiova, et al., "A randomised cross-over trial in healthy adults indicating improved absorption of omega-3 fatty acids by pre-emulsification", Nutrition Journal, vol. 6, Jan. 25, 2007.

Hibbeln, et al., "Maternal seafood consumption in pregnancy and neurodevelopmental outcomes in childhood (ALSPAC study): an observational cohort study", Lancet, vol. 369, Feb. 17, 2007, pp. 578-585.

Hong, et al., "Novel Docosatrienes and 17S-Resolvins Generated from Docosahexaenoic Acid in Murine Brain, Human Blood, and Glial Cells", The Journal of Biological Chemistry, vol. 278, Feb. 17, 2003, pp. 14677-14687.

Levy, et al., "Lipid mediator class switching during acute inflammation: signals in resolution", Nature Immunology, vol. 2, Jul. 2001, pp. 612-619.

Lewis, et al., "21 days of mammalian omega-3 fatty acid supplementation improves aspects of neuromuscular function and performance in male athletes compared to olive oil placebo", Journal of the International Society of Sports Nutrition, vol. 12, Jun. 18, 2015.

Lindmark, et al., "A 5-Month Open Study with Long-Chain Polyunsaturated Fatty Acids in Dyslexia", Journal of Medicinal Food, Dec. 2007, vol. 10, pp. 662-666.

Mazereeuw, et al., "Effects of ω-3 fatty acids on cognitive performance: a meta-analysis", Neurobiology of Aging, vol. 33, Feb. 3, 2012, pp. 1482.e17-1482.e29.

Mirnikjoo, et al., "Protein Kinase Inhibition by v-3 Fatty Acids", The Journal of Biological Chemistry, vol. 276, Apr. 6, 2001, pp. 10888-10896.

Oken, et al., "Maternal Fish Consumption, Hair Mercury, and Infant Cognition in a U.S. Cohort", Environmental Health Perspectives, vol. 113, May 26, 2005, pp. 1376-1380.

Philippoussis, et al., "Derivatives of monoglycerides as apoptotic agents in T-cells", Cell Death and Differentiation, vol. 8, Nov. 2001, pp. 1103-1112.

Raatz, et al., "Enhanced absorption of omega-3 fatty acids from emulsified compared with encapsulated fish oil", Journal of the American Dietetic Association, vol. 109, Jun. 2009, pp. 1076-1081.

Madiseh, et al., "Biochemical components of Berberis lycium fruit and its effects on lipid profile in diabetic rats", Journal of HerbMed Pharmacology, vol. 3, Jun. 2014, pp. 15-19.

Serhan, et al., "Lipoxins: Novel series of biologically active compounds formed from arachidonic acid in human leukocytes", Proceedings of the National Academy of Sciences of the United States of America, vol. 81, Sep. 1984, pp. 5335-5339.

Serhan, et al., "Novel Functional Sets of Lipid-derived Mediators with Antiinflammatory Actions Generated from Omega-3 Fatty Acids via Cyclooxygenase 2-Nonsteroidal Antiinflammatory Drugs and Transcellular Processing", The Journal of Experimental Medicine, vol. 192, Oct. 16, 2000, pp. 1197-1204.

Serhan, et al., "Resolvins: A Family of Bioactive Products of Omega-3 Fatty Acid Transformation Circuits Initiated by Aspirin Treatment that Counter Proinflammation Signals", The Journal of Experimental Medicine, vol. 196, Oct. 21, 2002, pp. 1025-1037.

Smithers, et al., "Higher dose of docosahexaenoic acid in the neonatal period improves visual acuity of preterm infants: results of a randomized controlled trial", American Journal of Clinical Nutrition, vol. 88, Oct. 2008, pp. 1049-1056.

Tavafi, et al., "Diabetic nephropathy and antioxidants", Journal of Nephropathology, vol. 2, Jan. 1, 2013, pp. 20-27.

Uauy, et al., "Nutrition in Brain Development and Aging: Role of Essential Fatty Acids", Nutrition Reviews, vol. 64, May 2006.

Uauy, et al., "Essential fatty acids in early life: structural and functional role", Proceedings of the Nutrition Society, vol. 59, Feb. 2000, pp. 3-15.

Yehuda, et al., "Essential Fatty Acids Are Mediators of Brain Biochemistry and Cognitive Functions", Journal of Neuroscience Research, vol. 56, Jun. 15, 1999, pp. 565-570.

Ikeda I, "Digestion and Absorption of Structured Lipids", Fat Digestion and Absorption, ed. Chrisyophe, A.G. & DeVriese S., Champaign: AOCS Press, 2000, pp. 235-243.

Morin, C., et al., "Anti-cancer effects of a new docosahexaenoic acid monoacylglyceride in lung adenocarcinoma", Recent Patents on Anti-Cancer Drug Discovery, vol. 8, Sep. 2013, pp. 319-334.

Birch, E.E., et al., "Visual Acuity and the Essentiality of Docosahexaenoic Acid and Arachidonic Acid in the Diet of Term Infants", Pediatric Research, vol. 44, Aug. 1, 1998, pp. 201-209.

Innis, S.M., "Essential fatty acid metabolism during early development.", Biology of Metabolism in Growing Animals, vol. 3, ed. D.G. Burrin & H.J. Mersmann, Amsterdam: Elsiever Science, 2005, pp. 235-274.

Giusto, et al., "Age-Associated Changes in Central Nervous System Glycerolipid Composition and Metabolism", Neurochemical Research, vol. 27, Nov. 2002, pp. 1513-1523.

Valaskova et al., "The influence of HLB on the encapsulation of oils by complex coacervation", Journal of Microencapsulation, Nov.-Dec. 1998, vol. 15, No. 6, pp. 747-751.

Nakagawa et al., "Microchannel emulsification using gelatin and surfactant-free coacervate microencapsulation", Journal of Colloid and Interface Science, Jun. 24, 2004, vol. 278, pp. 198-205.

(56) References Cited

OTHER PUBLICATIONS

C. Thies, "Microcapsules", C. Benjamin (Ed.), Encyclopedia of Food Sciences and Nutrition (Second Edition) (pp. 3892-3903). Oxford: Academic Press, Apr. 22, 2003.

* cited by examiner

PROCESS FOR THE PREPARATION AND STABILIZATION OF EMULSIONS WITH OMEGA-3 BY MEANS OF ISOMETRIC CRYSTALLINE NETWORKS OF CELLULOSE DERIVATIVES

CROSS-REFERENCE TO RELATED APPLICATIONS

The present patent application is a national phase application of International Application No. PCT/IB2016/055902, filed Oct. 3, 2016, which claims priority to Spanish Application No. 201531406, filed Oct. 1, 2015, the disclosures of which are incorporated herein by reference.

FIELD OF THE INVENTION

The present invention is framed within the field of specialized nutrition, both enteral clinical nutrition as well as dietetic and nutraceutical nutrition. The emulsions of the present invention may be used for preparing special medical foods required for complementing the nutritional needs in subjects who suffer from diseases with related dietetic deficiencies as well as nutritional supplements as complements for the diet, sports nutrition or child nutrition, amongst others.

BACKGROUND OF THE INVENTION

Emulsions are mixtures of various immiscible liquids. There are various types of emulsions, the two most common types of emulsions are oil in water (O/W) and water in oil (W/O). O/W emulsions are formed by an oily phase (apolar) dispersed in an aqueous phase (polar), while W/O emulsions relate to an aqueous phase dispersed in another oily type phase.

In general, emulsions are thermodynamically unstable systems and the phases which compose them tend to be separated by different mechanisms. However, emulsions may be kinetically stabilized, even for long periods of time, using two types of substances, emulsifiers and stabilizers which delay or prevent the destabilization mechanisms. The notion of stability is of course relative, but it relates to a near absence of change for a period of time that is sufficiently long for the purpose of practical application, which may vary from a few minutes to a few years.

The type of emulsion which is formed depends on the type of emulsifying agents used. When surfactants that are predominantly soluble in oil are used, W/O emulsions are formed and when surfactants that are soluble in water are used, they produce O/W emulsions, in accordance with an empirical rule (Bancroft rule) which allows the type of emulsions which will be formed to be predicted. There are in turn other systems characterized by the coexistence of oil in water (O/W) emulsions and water in oil (W/O) emulsions in which the globules of the dispersed phase contain within them smaller, similarly dispersed drops.

Taking into account the type of external and internal phase, emulsions may be classified within three categories, based on the internal phase percentage: low dispersed phase emulsions, medium dispersed phase emulsions and high dispersed phase emulsions.

Emulsions with a volume percent of internal phase below 25% are termed low ratio internal phase, emulsions which contain a percent of between 25% and 60% are termed medium ratio internal phase emulsions, and lastly emulsions with a content of between 60 and 70% of the total volume are termed high content internal phase emulsions. The volume percent of the internal phase has a significant influence on the properties of the emulsion, in fact in these last emulsions, the interactions between drops dominate the effects.

Low internal phase O/W emulsions are the emulsions that are most widely used commercially and are characterized by their low viscosity and by their Newtonian behavior in flow conditions.

In recent decades, O/W emulsions have been used for carrying active ingredients of different natures. In addition to the typical examples related to lactose products, mayonnaises, salad dressings and sauces, other more significant examples may be highlighted related to the controlled release of aromas (EP 1116515), liposoluble active ingredients such as conjugated linoleic acid (CA 2455226 C), erucic acid (U.S. Pat. No. 5,773,073 A), sterol esters (US 20060029622 A1) or phytosterols (WO 99/63841), vitamins with beta-carotene (U.S. Pat. No. 6,007,856 A), lycopene (WO 2014051116 A1), lutein (CN 104366508 A), zeaxanthin (US 20140170247 A1), vitamin A (U.S. Pat. No. 3,089,823 A) or D (U.S. Pat. No. 2,463,738 A), antioxidants such as for example tocopherols (EP 0868918 B1), flavonoids (WO 2011049629 A2), polyphenols (US 20090208472 A1) or curcumin (CN 100486567 C), nutraceuticals such as the coenzyme Q10 (US 20090142324 A1) and drugs such as benzodiazepine (WO 2003004015 A1) or mixtures of non-steroidal anti-inflammatories (U.S. Pat. No. 8,512,687 B2) amongst others.

The Omega-3 fatty acids are a family of polyunsaturated fatty acids, which include, amongst others, alpha linolenic acid (ALA), eicosapentaenoic acid (EPA), docosahexaenoic acid (DHA) and docosapentaenoic (n-3) acid (DPA). These are essential fatty acids which cannot be synthesized from other substances in mammals and therefore should be incorporated into the diet. ALA is converted into EPA and DHA in the organism, but the conversion rate is very low. Some sources with a high content of EPA and DHA are marine organisms, including, amongst others, fish such as for example salmon, anchovy, krill or algae, sources with a high content of ALA are for example nuts, chia seeds, hemp, flax or camelina, amongst others.

DHA is the most abundant Omega-3 fatty acid or (n-3) in the brain of mammals and the content thereof is modified depending on parameters such as the intake of different types of fatty acids and age, the content thereof reducing as age increases.

The nerves of the central and peripheral system contain predominantly polyunsaturated fatty acids. Omega-3 fatty acids are a component of the neurons, the nerve endings, myelin and the nuclear membranes (Bourre J et al, 1989).

Omega-3 fatty acids have neuroprotective properties and are an option in the treatment of various neurodegenerative diseases and neurological disorders. The administration of high doses of Omega-3 is associated with a reduced risk of Alzheimer's, (Mazereeuw G et. al., 2012). Beneficial effects in the treatment of clinical emotional disorders have also been tested with EPA (Dyall S C, 2015).

The suitable supply of Omega-3 polyunsaturated fatty acids is essential for the brain function: they increase the fluidity of the neuronal membranes and act as second messengers in the neurotransmission systems, in addition to contributing to many other aspects of the neuronal function (Mirnikjoo B et al, 2001; Yehuda S et al, 1999). DHA is involved in myelination (Durand G et al, 1999) and is important in synaptic efficiency (Uauy R et al, 2000) and in the speed of transmission (Yehuda S et al, 1999), which could increase efficiency in the processing of information. The effects of Omega-3s, especially DHA, in visual development and perception and even in dyslexia, may be related to the fact that they improve the photoreceptor function of the rods and visual sharpness and ensure the normal development of the retina in humans (Birch E E et al, 1992a; Birch E E et al, 1998). In relation to memory, in research on animals, it has been observed that DHA significantly affects the neuronal development of the hippocampus and the synaptic function in the hippocampus in developing neurons supplemented with DHA, the spontaneous synaptic activity is significantly greater and the fetuses of rats deprived of DHA show growth inhibition and synaptogenesis in the neurons of the hippocampus. These findings may explain the improvement of the cognitive processes after supplementation with DHA and why Omega-3 deficiency in the diet is associated with learning disability (Cao D et al, 2009). The speed with which the information is perceived and acquired depends, to a certain extent, on the presence of DHA (Cheatham C L et al, 2006).

The consumption of fish by the mother during pregnancy results in improved visual memory for recognizing new things and better results in the scoring of verbal or linguistic intelligence in children even after the age of 8 (Oken E et al, 2005; Hibbeln J R et al, 2007). The maternal consumption of supplements with 1200 mg of DHA and 800 of EPA is associated with higher scoring in standardized child intelligence tests (Oken E. et al, 2005). A suboptimal intake of fish by the mothers, below 340 mg/week, is associated with children situated in the lower quartile in verbal intelligence and in lower scores in scoring pro-social behavior, motor movements, communication and development of social skills (Hibbeln J R et al, 2007). Omega-3s may also be beneficial in children with learning difficulties, helping to improve reading speed in children who suffer from dyslexia (Lindmark L et al, 2007).

The majority of the lipids which are used in food, including Omega-3 fatty acids, are in the form of triglycerides (TG). The distribution and composition of the fatty acids in dietary triglycerides has an impact on the bioavailability thereof and consequently on the function thereof in the body. During digestion, the dietary triglycerides, upon encountering the gastrointestinal lipases, result in the formation of monoglycerides or monoacylglycerols (MAG) sn-2 (sn-2 refers to the position 2 of the glycerol) and two free fatty acids which are absorbed by the enterocytes. Once inside the enterocytes, the sn-2 MAG are reacylated once again to triglycerides and are released inside the lymphatic circulation via chylomicrons.

In the case of enzymatic deficiency, the administration of partially digested triglycerides, such as MAGs, may help the intraluminal solubilization and the absorption of the enterocytes. The monoglycerides may thus be identified as potential carriers of fatty acids in conditions of low activity with lipases (Cruz-Hernández C et al, 2012).

Generally the acids in the form of MAG are produced by esterification of free fatty acids with glyceryl followed by purification by short path distillation. Various isomers of MAG may be produced: sn-1(3)-MAG and sn-2-MAG. Unsaturated sn-2 MAG (of EPA and DHA) are not stable and are rapidly isomerized in order to produce sn-1(3)-MAG.

The Commission Regulation (EU) No. 432/2012 of 16 May 2012 establishes a list of authorized claims of healthy properties of the different foods of those related to reducing the risk, including some of the Omega-3 fatty acids, as can be seen in Table 1.

TABLE 1

Extract of the EU Regulation No. 432/2012

| Nutrient, substance, food or food category | Claim | Conditions of use of the claim | EFSA Journal number |
|---|---|---|---|
| Alpha-linolenic acid (ALA) | ALA contributes to the maintenance of normal blood cholesterol levels | The claim may be used only for food which is at least a source of ALA as referred to in the claim SOURCE OF OMEGA-3 FATTY ACIDS as listed in the Annex to Regulation (EC) No 1924/2006. Information shall be given to the consumer that the beneficial effect is obtained with a daily intake of 2 g of ALA. | 2009; 7(9): 1252 2011; 9(6): 2203 |
| Docosa-hexaenoic acid (DHA) | DHA contributes to maintenance of normal brain function | The claim may be used only for food which contains at least 40 mg of DHA per 100 g and per 100 kcal. In order to bear the claim information shall be given to the consumer that the beneficial effect is obtained with a daily intake of 250 mg of DHA | 2010; 8(10): 1734 2011; 9(4): 2078 |
| Docosa-hexaenoic acid (DHA) | DHA contributes to the maintenance of normal vision | The claim may be used only for food which contains at least 40 mg of DHA per 100 g and per 100 kcal. In order to bear the claim information shall be given to the consumer that the beneficial effect is obtained with a daily intake of 250 mg of DHA. | 2010; 8(10): 1734 2011; 9(4): 2078 |
| Eicosa-pentaenoic-acid and docosa-hexaenoic acid (EPA/DHA) | EPA and DHA contribute to the normal function of the heart | The claim may be used only for food which is at least a source of EPA and DHA as referred to in the claim SOURCE OF OMEGA-3 FATTY ACIDS as listed in the Annex to Regulation (EC) No 1924/2006. In order to bear the claim information shall be given to the consumer that the beneficial effect is obtained with a daily intake of 250 mg of EPA and DHA. | 2010; 8(10): 1796 2011; 9(4): 2078 |
| Linoleic acid | Linoleic acid contributes to the maintenance of normal blood cholesterol levels | The claim may be used only for a food which provides at least 1.5 g of linoleic acid (LA) per 100 g and per 100 kcal. Information shall be given to the consumer that the beneficial effect is obtained with a daily intake of 10 g of LA. | 2009; 7(9): 1276 2011; 9(6): 2235 |
| Oleic acid | Replacing saturated fats in the diet with unsaturated fats | The claim may be used only for food which is high in unsaturated fatty acids, as referred to in the claim HIGH UNSATURATED FAT | 2011; 9(4): 2043 |

TABLE 1-continued

Extract of the EU Regulation No. 432/2012

| Nutrient, substance, food or food category | Claim | Conditions of use of the claim | EFSA Journal number |
|---|---|---|---|
| | contributes to the maintenance of normal blood cholesterol levels. Oleic acid is an unsaturated fat. | as listed in the Annex to Regulation (EC) No 1924/2006. | |
| Mono-unsaturated and/or poly-unsaturated fatty acids | Replacing saturated fats with unsaturated fats in the diet contributes to the maintenance of normal blood cholesterol levels [MUFA and PUFA are unsaturated fats] | The claim may be used only for food which is high in unsaturated fatty acids, as referred to in the claim HIGH UNSATURATED FAT as listed in the Annex to Regulation (EC) No 1924/2006. | 2011; 9(4): 2069 2011; 9(6): 2203 |

The pro-resolving lipid mediators (SPMs or specialized pro-resolving mediators) are potent endogenous bioactive products derived from essential fatty acids which are synthesized by means of stereospecific and positional incorporation of one, two or three molecular oxygen molecules in the essential fatty acid, using as the substrate EPA, DHA, DPA or ARA in a catalytic reaction by fatty acid lipoxygenases, type 2 cyclooxygenases, acetylated by aspirin and various oxidases of cytochrome P450.

The primary lipid mediators derived from ARA were described by Serhan C N et al (Serhan C N et al, 1984) and the pro-resolution activity thereof was discovered by Dr. Serhan (Serhan C N et al, 2000; Levy et al, 2001). Therefore, the SPMs participate in the biological inflammation processes and constitute promising candidates for preparing drugs, nutraceuticals and hospital foods for treating inflammatory diseases and/or diseases or disorders in which an inflammatory response is manifested by the organism. Subsequently, other lipid mediators such as for example resolvins (Serhan C N et al, 2000) and protectins derived from DHA (Serhan C N et al, 2002; Hong S et al, 2003) and from EPA as well as maresins derived from DHA have been described. More recently, maresins, resolvins and protectins derived from DPA n-3 have been identified (Dalli et al, 2013).

The family of SPMs includes: lipoxin A4, 15-epi-lipoxin A4, lipoxin B4, 15-epi-lipoxin B4, RvE1, 18S-RvE1, 20-hydroxy-RvE1, RvE2, 18S-RvE2, 18S-RvE3, 18R-RvE3, MaR1, 7S-MaR1, 13R,14S-MaR2, 14S-hydroperoxy-DHA, PDX, 14S,21R-diHDHA, 14R,21S-diHDHA, 14R,21R-diHDHA, 14S,21S-diHDHA, 16,17-diHDHA, 16,17-Epoxy-DHA, 7,8-epoxy-17S-HDHA, PD1, 10S,17S-HDHA, 16,17S-diHDHA, 16,17-Epoxy-DHA, RvD1, RvD2, RvD3, RvD4, RvD5, RvD6, AT-Rv D1, AT-Rv-D2, AT-RvD3, AT-RvD4, 10S,17S-HDPAn-6, 17-HDPAn-6, 7,14-HDPAn-6, 10S,17S-HDPAn-6, 7,17-HDPAn-6, 15S-HETE, 15R-HETE, 5S-HEPE, 5R-HEPE, 11S-HEPE, 11R-HEPE, 12S-HEPE, 12R-HEPE, 15 S-HEPE, 15R-HEPE, 18S-HEPE, 18R-HEPE, 4S-HDHA, 7S-HDHA, 10S-HDHA, 11S-HDHA, 14S-HDHA, 14R-HDHA, 17S-HDHA, 17R-HDHA, 20S-HDHA, 17S-HDPAn-6, 14S-HDPAn-6, 10S-HDPAn-6, 17S-HDPAn-3, 14S-HDPAn-3, 10S-HDPAn-6, 17-HpDPAn-3, 17-hydroperoxy-DPAn-3, RvD1n-3DPA, RvD2 n-3DPA, RvD5 n-3DPA, PD1 n-3DPA, PD2 n-3DPA, 14-HpDHA, MaR1 n-3DPA, MaR2 n-3DPA y MaR3 n-3DPA, amongst others.

Marine oils: from fish, crustaceans, algae and mollusks have high levels of EPA, DPA and DHA Omega-3 polyunsaturated fatty acids, consequently they also have detectable levels of SPMs, these are promoted by way of the previously described biological routes. In addition, SPM-enriched oils may be obtained by means of purification processes described in the state of the art.

There are various commercial emulsions on the market which contain Omega-3 such as for example Incromega™, an Omega-3 emulsion which contains 250 mg of EPA+DHA per dose (5 g of emulsion) in the form of syrup or sachets. The Tegor Omega-3 emulsion is sold in 250 ml bottles and contains 800 mg of EPA and 400 mg of DHA per dose, in addition to vitamin C and E. Omelife™ Smooth DHA500 TG is an emulsion which contains Omega-3 with rapid bioavailability and produced with microencapsulation technology, this emulsion contains a minimum 70% of Omega-3 and a minimum 55% of DHA. Other Omega-3 emulsions which can be found on the market are OTEC™ 250CL-K or Nutegrity™.

The Smartfish emulsion is presented in 5 g sachets which contain 2250 mg of salmon oil, with a content of 630 mg of Omega-3, of which 245 mg are EPA and 245 mg are DHA.

Coromega® is an emulsion which contains 650 mg of Omega-3 in the form of triglyceride, which is presented in a dose of 2.5 g, of which 350 mg are EPA and 230 mg are DHA and which demonstrates greater absorption in a study carried out in 10 subjects compared with the consumption of an encapsulated equivalent oil (Raatz S K et al, 2009).

Omega Swirl from Barlean's is a liquid stabilized in the form of gel with the taste and texture of a smoothie which contains approximately 720 mg of EPA and DHA in the form of triglyceride per 15 milliliters of composition.

In addition, it has been demonstrated that the emulsification of the fish oil prevents the normal physiological step and increases the absorption thereof (Ikeda I et al, 2000), consequently designing emulsions which contain Omega-3 is one form of increasing the bioavailability of the same and the beneficial effects thereof. Garaiova I et al (Garaiova et al, 2007) reported an increase in the absorption of highly-unsaturated long-chain fatty acids and the incorporation thereof in plasmatic fatty acids upon administering pre-emulsified fish oil. Raatz S K et al, also reported similar short-term results when using an emulsified fish oil. The bioavailability of the emulsified oil is related to the particle size of the emulsion, consequently it is a crucial parameter when designing emulsions.

The derivatives of cellulose have traditionally been used as filling agents, some of which are unable to be metabolized, are binders in granulation processes or simply thickeners. Microcrystalline cellulose, for example has generally been used as a filling agent in low-calorie foods. Carboxymethyl cellulose is in turn mainly used for increasing the viscosity of foods. On other occasions, they have been used as single sources of insoluble dietary fiber.

More recently, other applications have been discovered for the synthetic derivatives of cellulose as a masking agent (CN104274836-A), food encapsulating material (WO2015104440-A1) or in the design of controlled release micro and nanocapsules (CN103432588-A), especially resistant to gastric digestion (WO2015102189 A1), designing bioadhesive compact matrices (EP 2344140 B1) and mucoadhesives polymers (UA99889-C2), as solid matrix disintegrating agents (US20150238424 A1) or boosters of the compressibility in pills and tablets (EP 2595611 A2).

Commercial emulsions do not have an ordered internal dynamic structure. The oil drops are dispersed in a liquid matrix (dispersion medium) in a disordered manner and it is normally assumed that they are statistically distributed, tending to coalesce with time. Many of them are also insoluble or hardly soluble in other liquid matrices, which together with the organoleptic defects related to the odor thereof of fish and the poor fluidodynamic characteristics which lead to increased residue in the mouth, make it difficult for the consumer to choose this form of taking Omega-3 oil.

In addition, commercial emulsions are not flexible or adaptable to the chemical form in which Omega-3 is found in the emulsion (monoglyceride, diglyceride, triglyceride, ethyl ester), to the ratio between them or to the proportion in which they are found. At the same time, final particle sizes below 1 micron and distribution of homogenous particle sizes are not easily achievable in commercial emulsions.

To date, the problem of preparing an emulsion on a large scale has not been resolved, characterized by a homogenous, ordered, structured and stable distribution of the oil microdrops and a suitable particle size which allows efficient absorption by the organism of oils with Omega-3 fatty acid and/or SPM content.

BRIEF DESCRIPTION OF THE INVENTION

In the research and development of oil in water (O/W) emulsions, the inventors of the present invention found that by means of activating and binding in the aqueous phase at least two cellulose derivatives, it is possible to structure and order an aqueous emulsions which, in the absence of these cellulosic derivatives, would contain oil in a disordered manner, being converted in an aqueous phase with an ordered microstructure similar to that of a three-dimensional cubic network.

An emulsion with these characteristics allows greater physical and chemical stability, increase of the bioavailability of the oils contained and improved gastro-resistance, all of which causing a controlled release of the Omega-3 fatty acids and optionally the pro-resolving lipid mediators (SPMs) contained in the emulsion, as well as less coalescence compared to other commercial emulsions.

In addition, the ordering of the oil microdrops of the emulsion within a three-dimensional network allows better control of the destabilization mechanisms (flocculation, sedimentation, etc.) inherent to any emulsion which allows emulsions to be designed with a greater guarantee of success in terms of stability.

Thus, in a first aspect, the present invention is directed at a novel oil in water (O/W) emulsion where the oil comprises Omega-3 fatty acids and which may also contain SPMs. Said emulsion is characterized by also comprising at least two cellulose derivatives and a hydrophilic emulsifier.

In a second aspect, the present invention relates to the method or process for preparing an oil in water (O/W) emulsion as it is defined above which comprises the following steps:
1) preparing an aqueous phase which comprises at least two cellulose derivatives;
2) activating the mixture of cellulose derivatives by vigorous stirring of the aqueous phase;
3) adding at least one hydrophilic emulsifier to the aqueous phase;
4) preparing an oily phase which comprises the oil that comprises the Omega-3 fatty acids;
5) mixing the aqueous phase and the oily phase, followed by homogenization.

In a third aspect, the present invention relates to an oil in water (O/W) emulsion that can be obtained according to the method described in the second inventive aspect.

In a fourth aspect, the present invention relates to the use of the emulsion as has been previously defined as a dietary supplement, nutraceutical product, medical food, pharmaceutical composition, medication, in sports nutrition, enteral and/or child nutrition.

DETAILED DESCRIPTION OF THE INVENTION

Figure 1:
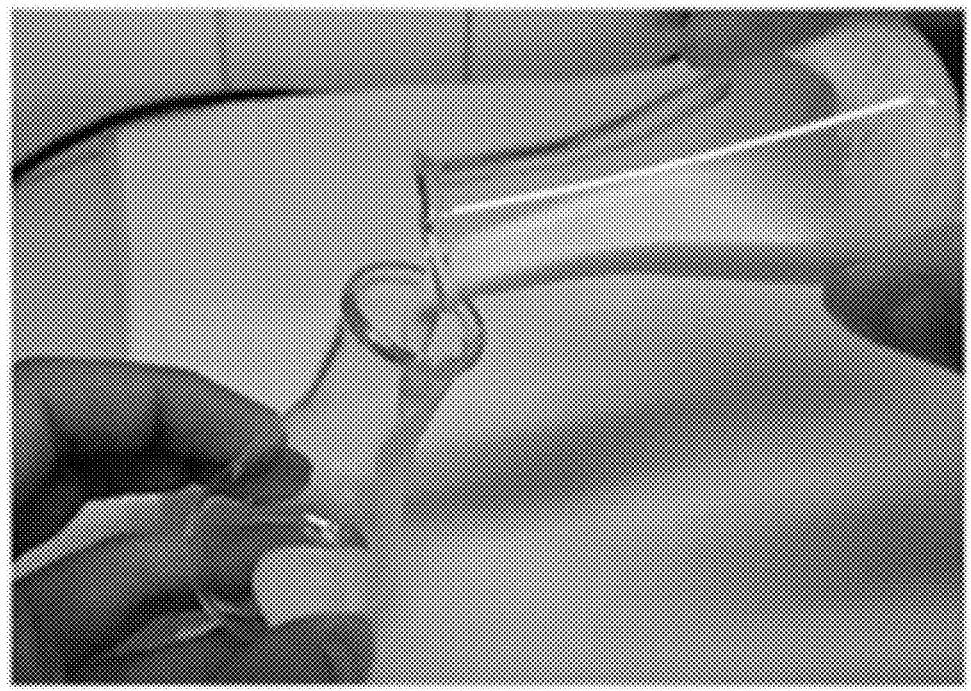
FIG. 1 shows a real image of the emulsion of the invention.

In a first aspect, the present invention relates to an oil in water (O/W) emulsion where the oil comprises Omega-3 fatty acids and where said emulsion also comprises at least two cellulose derivatives and at least one hydrophilic emulsifier.

In a particular embodiment, the at least two cellulose derivatives are bonded in the aqueous phase forming a three-dimensional network in which the oil is distributed.

In a more particular embodiment, the at least two cellulose derivatives are bonded in the aqueous phase forming an isometric crystalline network in which the oil is distributed.

The binding of the cellulose derivatives is produced by means of hydrogen bridge bonds between the hydroxyl groups and the oxygen atoms present in the polymeric chains of said derivatives. In order to obtain said bond, the cellulose derivatives must be previously activated. To this end, said derivatives are subjected to vigorous stirring in the aqueous phase, creating shearing forces which allows the hydration thereof in such a way that the interaction between contiguous chains is favored.

As a result of the activation and bond in the aqueous phase of the cellulose derivatives, it is possible to structure and order an aqueous emulsions which, in the absence of these cellulosic derivatives, would contain oil in a disordered manner, being converted in an aqueous phase with an ordered microstructure similar to that of a three-dimensional cubic network.

An emulsion with these characteristics allows greater physical and chemical stability, increase of the bioavailability of the acids contained and improved gastro-resistance, all of which causing a controlled release of the Omega-3 fatty acids and optionally the pro-resolving lipid mediators (SPMs) contained in the emulsion, as well as less coalescence compared to other commercial emulsions.

In addition, the ordering of the oil microdrops of the emulsion within a three-dimensional network allows better control of the destabilization mechanisms (flocculation, sedimentation, etc.) inherent to any emulsion which allows emulsions to be designed with a greater guarantee of success in terms of stability.

In a particular embodiment, the oil comprises at least 5% by weight of Omega-3 fatty acids.

In a particular embodiment, the cellulose derivatives are selected from microcrystalline cellulose, sodium carboxymethyl cellulose, ethyl hydroxyethyl cellulose, hydroxypropyl methyl cellulose (HPMC), hydroxyethyl methyl cellulose, hydroxypropyl cellulose (HPC), hydroxyethyl cellulose, ethyl methyl cellulose, ethyl cellulose, methyl cellulose, xanthan gum, guar gum and gum Arabic.

In a preferred embodiment, the cellulose derivatives are selected from microcrystalline cellulose, carboxymethyl cellulose and xanthan gum.

In a particular embodiment, the cellulose derivatives are selected from microcrystalline cellulose, sodium carboxymethyl cellulose, ethyl hydroxyethyl cellulose, hydroxypropyl methyl cellulose (HPMC), hydroxyethyl methyl cellulose, hydroxypropyl cellulose (HPC), hydroxyethyl cellulose, ethyl methyl cellulose, ethyl cellulose, methyl cellulose.

In a more preferred embodiment, the emulsion comprises two cellulose derivatives where said two derivatives are microcrystalline cellulose and carboxymethyl cellulose.

The microcrystalline cellulose, a purified and depolymerized cellulose, constitutes an example of cellulose derivative. It is a polysaccharide consisting of a linear chain from hundreds to thousands of D-glucose molecules bonded in a $\beta(1\rightarrow 4)$ manner. The multiple hydroxyl groups of a glucose chain form hydrogen bridge bonds with oxygen atoms of the same chain or with those of a neighboring chain, maintaining the chains in a solid manner, together side by side and forming microfibers with a large tensioning force.

Another example of cellulose derivative is carboxymethyl cellulose or carmellose, an organic compound, derived from cellulose, which is composed of carboxymethyl, bonded to hydroxyl groups and which is present in glucopyranose polymers.

In a preferred embodiment, the content of cellulose derivatives in the emulsion is less than 5% by weight with respect to the total weight of the emulsion.

In a more preferred embodiment, the content of cellulose derivatives in the emulsion is less than 4% by weight with respect to the total weight of the emulsion.

In a more preferred embodiment, the content of cellulose derivatives in the emulsion is less than 3% by weight with respect to the total weight of the emulsion.

In a more preferred embodiment, the content of cellulose derivatives in the emulsion is less than 2% by weight with respect to the total weight of the emulsion.

In an even more preferred embodiment, the content of cellulose derivatives in the emulsion is between 0.5% and 1.5% by weight with respect to the total weight of the emulsion.

The oil contained in the emulsion of the invention comprises Omega-3 fatty acids.

The Omega-3 fatty acids are a family of polyunsaturated fatty acids, which include, amongst others, alpha linolenic acid (ALA), eicosapentaenoic acid (EPA), docosahexaenoic acid (DHA) and docosapentaenoic (n-3) acid (DPA). These are essential fatty acids which cannot be synthesized from other substances in mammals and therefore should be incorporated into the diet. ALA is converted into EPA and DHA in the organism, but the conversion rate is very low. Some sources with a high content of EPA and DHA are marine organisms, including, amongst others, fish such as for example salmon, anchovy, krill or algae, sources with a high content of ALA are for example nuts, chia seeds, hemp, flax or camelina, amongst others.

In particular and within the context of the present invention, the oil of the emulsion is an oil extracted from a natural source which is enriched or has a high content of Omega-3 fatty acids.

In a particular embodiment, the oil which comprises the Omega-3 fatty acids of the emulsion of the invention may be obtained from sources of animal, vegetable or microbial origin, amongst others, such as for example fish oil, krill oil, vegetable oil, microbial oil and/or combinations of these.

In a particular embodiment of the invention, the oil which comprises the Omega-3 fatty acids of the emulsion is fish oil.

In another particular embodiment of the invention, the oil which comprises the Omega-3 fatty acids of the emulsion is krill oil.

In another particular embodiment of the invention, the oil which comprises the Omega-3 fatty acids of the emulsion is algae.

The oil which comprises the Omega-3 fatty acids of the emulsion comprises at least 1% by weight of eicosapentaenoic acid (EPA) and docosahexaenoic acid (DHA) with respect to the weight of the oil.

In a particular embodiment of the invention, the emulsion comprises at least 1% by weight of EPA and/or DHA with respect to the total weight of the oil.

In a particular embodiment of the invention, the emulsion comprises at least 5% by weight of EPA and/or DHA with respect to the total weight of the oil.

In another particular embodiment of the invention, the emulsion comprises at least 10% by weight of EPA and/or DHA with respect to the total weight of the oil.

In another particular embodiment of the invention, the emulsion comprises at least 15% by weight of EPA and/or DHA with respect to the total weight of the oil.

In another particular embodiment of the invention, the emulsion comprises at least 20% by weight of EPA and/or DHA with respect to the total weight of the oil.

In another particular embodiment of the invention, the emulsion comprises at least 25% by weight of EPA and/or DHA with respect to the total weight of the oil.

In another particular embodiment of the invention, the emulsion comprises at least 30% by weight of EPA and/or DHA with respect to the total weight of the oil.

In another particular embodiment of the invention, the emulsion comprises at least 35% by weight of EPA and/or DHA with respect to the total weight of the oil.

In another particular embodiment of the invention, the emulsion comprises at least 40% by weight of EPA and/or DHA with respect to the total weight of the oil.

In another particular embodiment of the invention, the emulsion comprises at least 45% by weight of EPA and/or DHA with respect to the total weight of the oil.

In another particular embodiment of the invention, the emulsion comprises at least 50% by weight of EPA and/or DHA with respect to the total weight of the oil.

In another particular embodiment of the invention, the emulsion comprises at least 1% by weight of DPA n-3 with respect to the total weight of the oil.

In another particular embodiment of the invention, the emulsion comprises at least 5% by weight of DPA n-3 with respect to the total weight of the oil.

In another particular embodiment of the invention, the emulsion comprises at least 10% by weight of DPA n-3 with respect to the total weight of the oil.

In another particular embodiment of the invention, the emulsion comprises at least 15% by weight of DPA n-3 with respect to the total weight of the oil.

In another particular embodiment of the invention, the emulsion comprises at least 5% by weight of DPA n-3 and/or EPA and/or DHA with respect to the total weight of the oil.

In another particular embodiment of the invention, the emulsion comprises at least 10% by weight of DPA n-3 and/or EPA and/or DHA with respect to the total weight of the oil.

In another particular embodiment of the invention, the emulsion comprises at least 15% by weight of DPA n-3 and/or EPA and/or DHA with respect to the total weight of the oil.

In another particular embodiment of the invention, the emulsion comprises at least 20% by weight of DPA n-3 and/or EPA and/or DHA with respect to the total weight of the oil.

In another particular embodiment of the invention, the emulsion comprises at least 25% by weight of DPA n-3 and/or EPA and/or DHA with respect to the total weight of the oil.

In another particular embodiment of the invention, the emulsion comprises at least 30% by weight of DPA n-3 and/or EPA and/or DHA with respect to the total weight of the oil.

In another particular embodiment of the invention, the emulsion comprises at least 35% by weight of DPA n-3 and/or EPA and/or DHA with respect to the total weight of the oil.

In another particular embodiment of the invention, the emulsion comprises at least 40% by weight of DPA n-3 and/or EPA and/or DHA with respect to the total weight of the oil.

In another particular embodiment of the invention, the emulsion comprises at least 45% by weight of DPA n-3 and/or EPA and/or DHA with respect to the total weight of the oil.

In another particular embodiment of the invention, the emulsion comprises at least 50% by weight of DPA n-3 and/or EPA and/or DHA with respect to the total weight of the oil.

The stability, which is provided by the isomeric crystalline network formed by the bond of cellulose derivatives to the emulsion of the invention, allows different types of chemical forms of Omega-3 fatty acids to be incorporated.

In fish oil, the Omega-3 fatty acids are mainly found in the form of triglycerides. The Omega-3 fatty acids may be converted into other chemical forms such as ethyl esters (EE), monoglycerides (MAG), diglycerides (DG), phospholipids or free fatty acids (FFA), amongst others, using methods widely known in the state of the art, using chemical process, such as for example by means of the transesterification of triglycerides with a $C_1$-$C_8$ alkyl alcohol such as for example methanol, ethanol, propanol, isopropanol, also forming phospholipids, preferably phosphoglycerides or by means of enzymatic processes with transesterification enzymatic reactions. The Omega-3 fatty acids may be concentrated and fractioned in specific compounds such as for example EPA, DHA and/or DPA n-3 in a selective manner, using methods for separation and extraction widely described in the state of the art and accessible to a person skilled in the art.

In the present invention, the term "$C_1$-$C_8$ alkyl" or "alkyl $C_1$-$C_8$" relates to aliphatic, linear or branched chains which contain 1 to 8 carbon atoms, preferably between 2 and 4 carbon atoms, such as for example, but not limited to, ethyl, n-propyl, i-propyl, n-butyl, n-pentyl or n-hexyl.

In a particular embodiment, the oil contained in the emulsion of the invention comprises Omega-3 fatty acids in the form of $C_1$-$C_8$ alkyl ester.

In a particular embodiment, the oil contained in the emulsion of the invention comprises Omega-3 fatty acids in the form of ethyl ester.

In a particular embodiment, the oil contained in the emulsion of the invention comprises Omega-3 fatty acids in the form of phospholipid.

In a particular embodiment, the oil contained in the emulsion of the invention comprises Omega-3 fatty acids in the form of phosphoglyceride.

In a particular embodiment, the oil contained in the emulsion of the invention comprises Omega-3 fatty acids in the form of triglyceride.

In another particular embodiment, the oil contained in the emulsion of the invention comprises at least 60% by weight, with respect to the oil, of the Omega-3 fatty acids in the form of triglycerides.

In a particular embodiment, the oil contained in the emulsion of the invention comprises Omega-3 fatty acids in the form of free fatty acids, esters, phospholipids, monoglycerides, diglycerides, triglycerides and/or combinations of these.

In a more particular embodiment, the oil contained in the emulsion of the invention comprises Omega-3 fatty acids in the form of triglyceride and a mixture of partial glycerides (monoglycerides and diglycerides).

The Omega-3 MAG (monoglyceride or monoacylglyceride) fatty acids are absorbed by the gastrointestinal tract, they are not toxic and the metabolites thereof are found in blood circulation and in the tissues (Morin C et al, 2013; PCT/CA2008/000530, PCT/CA2008/000301). Philippoussis et al have demonstrated that the lipids in the form of MAG induce the apoptosis in the T cells better compared to the corresponding free fatty acids (Philippoussis F et al, 2001). Consequently, in determined conditions, the administration of the Omega-3 fatty acid in the form of MAG may have an advantage over other chemical forms of administration of the Omega-3 fatty acids, due to the improved absorption and the use thereof is therefore more efficient.

In a particular embodiment, the oil contained in the emulsion of the invention comprises Omega-3 fatty acids in the form of monoglyceride.

In another particular embodiment, the oil contained in the emulsion of the invention comprises at least 40% by weight, with respect to the oil, of Omega-3 fatty acids in the form of monoglyceride.

In a particular embodiment of the invention, the oil of the emulsion also comprises at least one pro-resolving lipid mediator (SPM).

The pro-resolving lipid mediators (SPMs or specialized pro-resolving mediators) are potent endogenic bioactive products derived from essential fatty acids which are synthesized by means of stereospecific and positional incorporation of one, two or three molecular oxygen molecules in the essential fatty acid, using as the substrate EPA, DHA, DPA or ARA in a catalytic reaction by fatty acid lipoxygenases, type 2 cyclooxygenases, acetylated by aspirin and various oxidases of cytochrome P450.

In a preferred embodiment, the SPM is selected from lipoxin A4, 15-epi-lipoxin A4, lipoxin B4, 15-epi-lipoxin B4, RvE1, 18S-RvE1, 20-hydroxy-RvE1, RvE2, 18S-RvE2, 18S-RvE3, 18R-RvE3, MaR1, 7S-MaR1, 13R,14S-MaR2, 14S-hydroperoxy-DHA, PDX, 14S,21R-diHDHA, 14R, 21S-diHDHA, 14R,21R-diHDHA, 14S,21S-diHDHA, 16,17-diHDHA, 16,17-Epoxy-DHA, 7,8-epoxy-17S-HDHA, PD1, 10S,17S-HDHA, 16,17S-diHDHA, 16,17-Epoxy-DHA, RvD1, RvD2, RvD3, RvD4, RvD5, RvD6, AT-Rv D1, AT-Rv-D2, AT-RvD3, AT-RvD4, 10S,17S-HDPAn-6, 17-HDPAn-6, 7,14-HDPAn-6, 10S,17S-HDPAn-6, 7,17-HDPAn-6, 15S-HETE, 15R-HETE, 5S-HEPE, 5R-HEPE, 11S-HEPE, 11R-HEPE, 12S-HEPE, 12R-HEPE, 15 S-HEPE, 15R-HEPE, 18S-HEPE, 18R-HEPE, 4S-HDHA, 7S-HDHA, 10S-HDHA, 11S-HDHA, 14S-HDHA, 14R-HDHA, 17S-HDHA, 17R-HDHA, 20S-HDHA, 17S-HDPAn-6, 14S-HDPAn-6, 10S-HDPAn-6, 17S-HDPAn-3, 14S-HDPAn-3, 10S-HDPAn-6, 17-HpDPAn-3, 17-hydroperoxy-DPAn-3, RvD1n-3DPA, RvD2 n-3DPA, RvD5 n-3DPA, PD1 n-3DPA, PD2 n-3DPA, 14-HpDHA, MaR1 n-3DPA, MaR2 n-3DPA, MaR3 y n-3DPA, and mixtures of the same.

The IUPAC names of these SPMs are described in US 2015/0126602 A1.

In a more preferred embodiment, the SPM is selected from 18R/S-HEPE, 17R/S-HDHA, 5S-HEPE, 15RS-HEPE, 4R/S-HDHA, 7R/S-HDHA, 10R/S-HDHA, 14R/S-HDHA and RvE1 and mixtures of the same.

In another more preferred embodiment, the SPM is 17S/R-HDHA.

In another more preferred embodiment, the SPM is 18R/S-HEPE.

In another even more preferred embodiment, the pro-resolving lipid mediators (SPMs) are 17S/R-HDHA and 18S/R-HEPE.

In another even more preferred embodiment, the emulsion comprises between 0.0005% and 1% by weight of 17S/R-HDHA and 18S/R-HEPE where the percentage by weight is with respect to the total weight of the emulsion.

In another even more preferred embodiment, the emulsion comprises between 0.0005% and 1% by weight of 17S/R-HDHA, 18S/R-HEPE and 14R/S-HDHA, where the percentage by weight is with respect to the total weight of the emulsion.

In a particular embodiment, the emulsion of the invention is characterized in that it comprises:
1) 1.0 to 40% by weight of oil which comprises Omega-3 fatty acids;
2) 0.1 to 5.0% by weight of cellulose derivatives;
3) 0.1 to 10% by weight of hydrophilic emulsifier;
where all the percentages by weight are based on the total weight of the emulsion.

In a more preferred embodiment, the emulsion of the invention is characterized in that it comprises:
1) 1.0 to 30% by weight of oil which comprises Omega-3 fatty acids;
2) 0.4 to 1.5% by weight of cellulose derivatives;
3) 0.2 to 3.0% by weight of hydrophilic emulsifier;
where all the percentages by weight are based on the total weight of the emulsion.

With the aim of facilitating the stability of the emulsion of the invention, it may contain at least one hydrophilic emulsifier.

In a particular embodiment, the hydrophilic emulsifier is selected from polyoxyethylene (20) sorbitan monolaurate, polyoxyethylene (20) sorbitan monopalmitate, polyoxyethylene (20) sorbitan monosterate, polyoxyethylene (20) sorbitan tristearate, polyoxyethylene (20) sorbitan monooleate, monoacetyl tartaric and diacetyl tartaric esters of mono and diglycerides of fatty acids and citric esters of mono and diglycerides of fatty acids and mixtures of the same.

In a more preferred embodiment, the emulsifier is selected from polyoxyethylene (20) sorbitan monooleate, monoacetyl tartaric and diacetyl tartaric esters of mono and diglycerides of fatty acids and citric esters of mono and diglycerides of fatty acids.

With the aim of stabilizing the emulsion of the invention microbiologically, it may contain one or various food preservatives such as for example, but not being limited to, sorbic acid, potassium sorbate, benzoic acid, sodium benzoate, propyl hydroxybenzoate, methyl hydroxybenzoate and/or nisin.

In a particular embodiment, the emulsion of the present invention comprises at least one preservative.

In a more preferred embodiment, the preservative or preservatives are selected from potassium sorbate, sodium benzoate, propyl hydroxybenzoate and methyl hydroxybenzoate.

In an even more preferred embodiment, the preservative is potassium sorbate and/or potassium benzoate.

With the aim of improving the organolepsy of the emulsion of the present invention and of the active ingredients which it contains, the emulsion of the invention may comprise at least one food sweetener such as for example, but not being limited to, sucralose, xylitol, stevia and ecological cane sugar and/or at least one aroma such as for example, but not being limited to, lemon oil, peppermint oil, pineapple aroma, coconut oil, orange aroma, mango aroma, lime aroma, peach aroma and/or clementine aroma.

In a particular embodiment, the emulsion comprises at least one sweetener.

In a preferred embodiment, the sweetener is sucralose and/or xylitol.

In a particular embodiment, the emulsion contains at least one aroma.

In a preferred embodiment, the aroma or aromas are selected from lemon oil, peppermint oil, pineapple aroma, coconut oil, orange aroma, mango aroma, lime aroma, peach aroma and/or clementine aroma.

In a more preferred embodiment, the aroma is lemon oil and/or peppermint oil.

The emulsion of the invention may contain at least one antioxidant.

In a preferred embodiment, the antioxidant is selected from curcumin, demethoxycurcumin, bisdemethoxycurcumin, tetrahydrocurcumin, vitamin E (tocopherol), vitamin C (ascorbic acid), derivatives of ascorbic acid and/or rosemary extract and the derivatives thereof.

In a more preferred embodiment, the antioxidant is curcumin.

Turmeric is an herbaceous plant of the Zingiberaceae family originally from south Asia, mainly from India and is rich in curcumin, a polyphenol traditionally used in Ayurveda medicine and in the European Union it is authorized as a food additive in a maximum concentration of 0.05 g/100 g (E-100i). Various tests have shown that curcumin has antioxidant, anti-cancerous effects and anti-inflammatory properties (Ardalan M et al, 2014; Tavafi M, 2013; Barandaran A, 2012; Rahimi-Madiseh M et al, 2014). Derivatives of curcumin with similar properties have been described, such as for example demethoxycurcumin, bisdemethoxycurcumin and tetrahydrocurcumin.

In a particular embodiment, the emulsion contains a pharmaceutically acceptable carrier.

In another particular embodiment, the emulsion is soluble in an aqueous solution.

The process for preparing the emulsion of the invention allows emulsions with a particle size of between 400 nanometers (nm) and 2000 nm to be obtained, depending on the homogenization process used which increases the bioavailability of the Omega-3 fatty acids and, where appropriate, also the SPMs.

In a particular embodiment, the emulsion has a particle size of between 500 and 2000 nm.

In a preferred embodiment, the emulsion has a particle size of between 600 and 1300 nm.

The ordered structuring of the emulsion of the invention by means of the bond of the cellulose derivatives gives stability to the emulsion and in addition, allows the emulsion to be capable of being adapted to different needs of the market, emulsions with different tastes and with textures, which allow easy ingestion of the emulsion, can be designed.

In a second aspect, the invention includes a method or process for preparing the emulsion of the invention by means of mixing an aqueous phase which comprises at least two types of cellulose derivatives and a hydrophilic emulsifier with an oily phase which, in turn, comprises Omega-3 fatty acids and, where appropriate, also SPMs.

In a particular embodiment, the method or process for preparing an emulsion of the invention comprises the following steps:
1) preparing an aqueous phase which comprises at least two cellulose derivatives;
2) activating the mixture of cellulose derivatives by vigorous stirring of the aqueous phase in order to facilitate the bond of said derivatives and thereby form an ordered microstructure;
3) adding at least one hydrophilic emulsifier to the aqueous phase;
4) preparing an oily phase which comprises the oil that comprises the Omega-3 fatty acids and
5) mixing the aqueous phase and the oily phase, followed by homogenization.

In a preferred embodiment, the aqueous phase also comprises preservatives, such as for example and without being limited to sorbates such as for example potassium sorbate, sodium sorbate or benzoates such as for example sodium benzoate or calcium benzoate amongst others and sweeteners such as for example sucralose, stevia, ecological cane sugar or xylitol amongst others using mechanical stirring. Said components are added to the aqueous phase prior to incorporating the cellulose derivatives.

In this aqueous phase, the mixture of at least two cellulose derivatives, which are activated by means of mechanical stirring at a preferably high velocity, is added followed by the addition of a hydrophilic emulsifier.

The oily phase is prepared from the oil obtained by extraction from a natural source and which comprises the Omega-3 fatty acids and, where appropriate, also the SPMs.

In a particular embodiment, aromas are added to the oily phase such as peppermint aroma, lemon aroma, pineapple aroma, coconut oil, orange aroma, mango aroma, lime aroma, peach aroma, clementine aroma amongst others and the antioxidants such as curcumin, demethoxycurcumin, bisdemethoxycurcumin, tetrahydrocurcumin, vitamin E (tocopherol), vitamin C (ascorbic acid), derivatives of ascorbic acid, rosemary extract and the derivatives thereof, stirring said mixture.

The oily phase and the aqueous phase are mixed and homogenized until a homogenous emulsion is achieved.

In a particular embodiment, the oily phase and the aqueous phase are emulsified by means of mechanical stirring at room temperature for at least 30 minutes.

Lastly and if necessary, the emulsion may be pasteurized by heating approximately to 75° C. for at least 5 seconds with stirring.

Finally, the pH of the emulsion is adjusted, using an acidulent, for example but not being limited to sodium citrate.

In a particular embodiment, the emulsion of the invention is stable between 2 and 80°.

In a particular embodiment, the emulsion of the invention is stable between 3 and 50°.

In a particular embodiment, the emulsion of the invention is stable between 3 and 25°.

In a third aspect, the invention relates to an oil in water (O/W) emulsion that can be obtained according to the method of the invention where the rest of the components such as those which have been previously defined may be incorporated.

Said method allows an emulsion to be obtained which is characterized by being structured in an isomeric crystalline network of cellulose derivatives, formed by a mixture of at least two types of cellulose derivatives which allow the homogeneous distribution of the oil which comprises the Omega-3 fatty acids in a three-dimensional structure, which allows greater stability, bioavailability and gastro-resistance (controlled release) of the Omega-3 oil of the emulsion as well as less coalescence compared to commercial emulsions. Furthermore, said method for preparing the emulsion of the invention allows emulsions to be obtained with a particle size of between 400 nanometers (nm) and 2000 nm depending on the homogenization process used which increases the bioavailability of the Omega-3 fatty acids and, where appropriate, also the SPMs and is soluble in water.

In a forth inventive aspect, the invention relates to the use of the emulsion as has been previously defined as a dietary supplement, nutraceutical product, medical food, pharmaceutical composition, medication, in sports nutrition, enteral and/or child nutrition.

In a particular embodiment, the invention relates to the use of the emulsion as has been previously described in enteral nutrition.

Enteral nutrition is carried out when voluntary oral feeding is not possible by way of a tube, removing the passage through the oral cavity and esophagus such that administration can take place directly via different sections of the digestive tract such as the stomach, duodenum or jejunum.

The enteral route of administration makes reference to administration by the oral, sublingual, gastroenteric or rectal route. The oral route makes reference to administration through the oral cavity to the stomach or the proximal portion of the small intestine, subsequently passing through the intestinal wall and the liver.

In a preferred embodiment, the emulsion of the invention may be may be administered by the oral route. The emulsion of invention may also be mixed with other liquids such as juices, yogurts, smoothies, milk or infusions amongst others prior to its oral administration.

In another particular embodiment, the emulsion of the invention may be administered by the gastroenteric route through a tube, acting as a nutritional medium for subjects who cannot be fed by the oral route.

The emulsion of the invention may be included in different forms of presentation adapted to the different uses, such as for example sachets, in the form of syrup, in plastic or glass jars or bottles and drinkable vials amongst others.

In a particular embodiment, the emulsion of the invention may be presented in the form of sachets.

In another particular embodiment, the emulsion of the invention may be presented in plastic or glass bottles.

In another particular embodiment, the emulsion of the invention may be presented in plastic or glass jars.

In a particular embodiment, the emulsion of the invention may be presented in plastic or glass drinkable vials.

In an additional aspect, the invention relates to the use of the emulsion as has been previously defined as a dietary supplement, nutraceutical product, in sports or child nutrition, medical food and/or a pharmaceutical composition.

In a preferred embodiment, the invention relates to the use of the emulsion as has been previously defined as a dietary supplement, nutraceutical product, medical food and/or a pharmaceutical composition.

In a particular embodiment, the invention relates to the use of the emulsion as has been previously defined as a food or dietary supplement.

Food or dietary supplements are preparations which are administered by the oral route, intended to complement food and which contain a "food ingredient" such as for example vitamins, minerals, fatty acids such as Omega-3 fatty acids or plant extracts amongst others and which act as a complement to the diet and not as substitutes for a conventional food.

In a particular embodiment, the invention relates to the use of the emulsion as has been previously defined as a nutraceutical product.

Nutraceutical products are produced from substances which are present in natural form in determined foods and which have a beneficial effect on health, with a preventative and/or therapeutic capacity with respect to a disease or condition.

Omega-3 fatty acids have health properties as is reflected in the authorized claim of the Commission Regulation (EU) No. 432/2012 of 16 May 2012 summarized in Table 1. In particular, EPA and DHA acids contribute to the normal function of the heart with a daily intake of 250 mg of EPA and DHA. DHA contributes to maintaining vision in normal conditions and contributes to maintaining the normal function of the brain with a daily intake of 250 mg of DHA.

In a particular embodiment, the invention relates to the use of the emulsion as has been previously described in child nutrition.

Various studies associate DHA with the neurological and visual development of children. There are numerous supplementation assays with long-chain polyunsaturated fatty acids (LC-PUFA) in premature children which have obtained results which show greater visual sharpness following a diet supplemented with DHA compared to a placebo (Birch et al, 1992b; Carlson et al, 1993; Smithers et al, 2008).

In a particular embodiment, the invention relates to the use of the emulsion as has been previously defined in sports nutrition.

The ability of the muscles to produce force and resistance to fatigue are essential qualities for sports activity. The adaptations of the neuromuscular system and the muscles which are produced by training are those responsible for modulating the force and resistance to fatigue. This has involved determining the effect of various nutritional supplements such as for example supplementing with proteins, adapting the muscles to force training or the use of carbohydrates in improving the resistance. More recent studies have determined that supplementing with Omega-3 improves the peripheral neuromuscular function and aspects related to fatigue in male athletes.

In a particular embodiment, the invention relates to the use of the emulsion as has been previously described as a medical food.

A medical food is a food which is formulated to be consumed orally or enterically administered under the supervision of a doctor and which is intended for the specific dietary management of a disease or disorder for which, after a medical evaluation, different nutritional requirements have been established, based on recognized scientific principles. Thus medical foods are especially formulated and processed (unlike a food used in its natural state) to be supplied to a very sick patient or who requires the use of the product as an important component for the specific dietary management of the disease or condition which they suffer. A medical food combines the following characteristics:

a) It is a product especially formulated and processed for partial or exclusive feeding of a patient through the oral route or through a gastrointestinal tube.

b) It is intended for the dietary management of a patient who, due to chronic or therapeutic needs, has a limited or restricted capacity for ingesting, digesting, absorbing or metabolizing common foods or certain nutrients or who has requirements for nutrients which cannot be solved by modifying the normal diet.

c) It provides a nutritional support specifically modified for managing a single nutrient which their specific disease requires as determined by a medical evaluation.

d) It should be used under medical supervision.

e) It is directed at patients who are receiving an active treatment with frequent contact with the doctor, from whom they receive specific instructions regarding the use of the food.

In various particular embodiments, the invention relates to the use of the emulsion as has been previously defined for preparing a medical food for the specific dietary management of a disease or disorder with an inflammatory component.

In a particular embodiment, the emulsion of the invention may be used for preparing a pharmaceutical composition which also comprises at least one excipient, adjuvant and/or pharmaceutically acceptable carrier.

The pharmaceutical compositions which contain a therapeutically effective quantity of the emulsion of the present invention together with the pharmaceutically acceptable carriers constitute an additional aspect of the present invention.

The term "pharmaceutically acceptable carrier" relates to a diluent, adjuvant or excipient by means of which the active ingredient is administered. Such pharmaceutical carrier may be sterile liquids, such as water and oils including those with an oil, animal, vegetable or synthetic origin such as peanut oil, soya oil, mineral oil, sesame oil and similar. They are preferably used as water carriers or aqueous solutions of saline solution. Preferably, the carriers of the invention are approved by the regulatory agency of a state or federal government or they are listed in the United States Pharmacopeia, in the European Pharmacopeia or in any recognized pharmacopeia in general for the use thereof in animals and particularly in humans.

In various particular embodiments, the emulsion of the invention may be used for manufacturing a medication useful for the enteral route of administration thereof to a subject for treating a disease or disorder which presents an inflammatory component by administering the therapeutically effective dose.

The diseases which cause an inflammatory component may be selected from: Crohn's disease, IBD, fatty liver, wound healing, arterial inflammation, arthritis, psoriasis, urticarial, vasculitis, asthma, ocular inflammation, pulmonary inflammation, dermatitis, cardiovascular diseases, AIDS, Alzheimer's, atherosclerosis, cancer, type 2 diabetes, hypertension, neuromuscular disorders, obesity, infectious diseases, leukemia, lymphoma, metabolic syndrome, obesity, heart attack, rheumatism, transplants, periodontal diseases, brain damage, trauma, cystic fibrosis and muscular disorders.

According to the present description, the use of the emulsion of the invention or a pharmaceutical composition of the same for manufacturing a medication or alternatively the use thereof as a medication for treating a disease or disorder which presents an inflammatory component may be obviously understood as a treatment method of such disease or disorder which comprises the administration to a subject of a therapeutically effective quantity of said emulsion or pharmaceutical composition of the same. In other words, the present invention also relates to a method for treating a disease or disorder (preferably selected from: Crohn's disease, IBD, fatty liver, wound healing, arterial inflammation, arthritis, psoriasis, urticarial, vasculitis, asthma, ocular inflammation, pulmonary inflammation, dermatitis, cardiovascular diseases, AIDS, Alzheimer's, atherosclerosis, cancer, type 2 diabetes, hypertension, neuromuscular disorders, obesity, infectious diseases, leukemia, lymphoma, metabolic syndrome, obesity, heart attack, rheumatism, transplants, periodontal diseases, brain damage, trauma, cystic fibrosis and muscular disorders) which comprises administering the emulsion of the invention to the subject in a therapeutically effective quantity, or a pharmaceutical composition of the invention.

The use of the values specified in this application should be understood, unless otherwise expressly indicated, as approximations to said values. The numeric values of the application represent various particular embodiments of the invention, but should not be considered as limiting of the same.

EXAMPLES

In the present invention, the content of Omega-3 fatty acids in the emulsion is expressed as percentage by weight with respect to the total weight of the emulsion and is determined by firstly extracting the oil from the emulsion and subsequently measuring the content by means of the methods as they are described in the monograph of the Omega-3 fatty acids of the European Pharmacopeia, method 2.49.29 or any other equivalent method using gas chromatography, HPLC, FPLC or any other chromatographic method and they are expressed as a percentage in the form of free fatty acids (FFA), unless anything else is explicitly expressed.

Example 1. Industrial Production of an Emulsion with Omega-3 Fatty Acids (Ethyl Ester)

In order to carry out the industrial production of 95 kg of an Omega-3 fatty acid emulsion in the form of ethyl ester (EE) in water (EMOX-1), two phases were prepared at room temperature, an aqueous phase and an oily phase, which were mixed and were emulsified. Table 2 shows the composition of the emulsion.

The aqueous phase was obtained by mixing water, preservatives (potassium sorbate and sodium benzoate) and sweeteners (sucralose) under mechanical stirring. In this aqueous phase, the mixture of cellulose derivatives (88% microcrystalline cellulose and 12% carboxymethyl cellulose), which was activated by means of vigorous stirring, and hydrophilic emulsifier (monoacetyl tartaric and diacetyl tartaric esters of mono and diglycerides of the fatty acids) was also added. The aqueous phase was stirred at room temperature for approximately 10 minutes.

In order to prepare the oily phase, the oil (80/00EE) was used which is a semi-refined fish oil esterificated as ethyl ester (EE), concentrated to 80% EPA and lastly deodorized, in addition to containing vitamin E as an antioxidant. The oil (80/00EE), which comprises the Omega-3 fatty acids in the form of ethyl ester, was mixed with the aromas (lemon oil concentrate and peppermint aroma) and the mixture was stirred at room temperature.

The oily and aqueous phase were mixed and emulsified by means of mechanical stirring for approximately 30 minutes at room temperature. Following emulsification, the mixture was subjected to a pasteurization process for which the emulsified mixture was heated to 75° C. for approximately 7 seconds. After this time, the pH was adjusted with trisodium citrate and the emulsion was preferably cooled at a temperature below 25° C.

TABLE 2

| Composition of EMOX-1 | |
|---|---|
|  | Composition (% by weight) |
| Omega-3 fatty acids | 25 |
| Aroma (lemon and peppermint oil) | 1.57 |
| Mixture of celluloses (88% microcrystalline cellulose and 12% carboxymethyl cellulose) | 0.8 |
| Hydrophilic emulsifier | 2 |
| Preservatives (potassium sorbate and sodium benzoate) | 0.04 |
| Sucrelose | 0.02 |
| Trisodium citrate | Depending on the final pH |
| Water | csp 100 |

The technical analysis of the EMOX-1 emulsion is included in Table 3.

TABLE 3

| EMOX-1 technical analysis sheet | | |
|---|---|---|
| Determination | Specification | Method |
| Fatty acid profile (expressed as FFA) | | |
| EPA (mg/g) | Min 180.0 | Eur. Ph. 2.49.29 |
| Omega-3 total (mg/g) | Min 193.3 | Eur. Ph. 2.49.29 |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| *Escherichia Coli* (CFU/g) | Absent | Eur. Ph. 2.6.13 |
| *Staphylococcus aureus* (CFU/g) | Absent | Eur. Ph. 2.6.13 |
| *Salmonella* spp (CFU/10 g) | Absent | Eur. Ph. 2.6.13 |

Example 2. Industrial Production of an Emulsion with Omega-3 Fatty Acids (Triglyceride)

In order to carry out the industrial production of 95 kg of an Omega-3 fatty acid emulsion in the form of triglyceride in water (EMOX-2), two phases were prepared at room temperature, an aqueous phase and an oily phase, which were subsequently mixed and were emulsified. Table 4 shows the composition of the emulsion.

The aqueous phase was obtained by mixing water, preservatives (potassium sorbate and sodium benzoate) and sweeteners (sucralose and xylitol) under mechanical stirring. In this aqueous phase, the mixture of cellulose derivatives (88% microcrystalline cellulose and 12% carboxymethyl cellulose), which was activated by means of vigorous stirring, and hydrophilic emulsifier (citric esters of mono and diglycerides of the fatty acids) was also added. The aqueous phase was stirred at room temperature for approximately 10 minutes.

In order to prepare the oily phase, the oil (18/12 TG) was used which is a natural refined and deodorized fish oil (anchovy/sardine) which contains vitamin E as an antioxidant. The oil (18/12 TG), which comprises 18% EPA and 12% DHA largely in the form of triglyceride (TG), was mixed with the aromas (pineapple aroma and coconut oil) and the mixture was stirred at room temperature.

The oily and aqueous phase were mixed and emulsified by means of mechanical stirring for approximately 30 minutes at room temperature. Following emulsification, the mixture was subjected to a pasteurization process for which the emulsified mixture was heated to 75° C. for approximately 7 seconds. After this time, the pH was adjusted with trisodium citrate and the emulsion was preferably cooled at a temperature below 25° C.

TABLE 4

| Composition of EMOX-2 | |
| --- | --- |
| | Composition (% by weight) |
| Omega-3 fatty acids | 25 |
| Aroma (pineapple aroma and coconut oil) | 5 |
| Mixture of celluloses (88% microcrystalline cellulose and 12% carboxymethyl cellulose) | 0.66 |
| Hydrophilic emulsifier | 3 |
| Preservatives (potassium sorbate and sodium benzoate) | 0.04 |
| Sweetener (sucralose and xylitol) | 1.02 |
| Trisodium citrate | Depending on the final pH |
| Water | csp 100 |

The technical analysis of the EMOX-2 emulsion is included in Table 5.

TABLE 5

| EMOX-2 technical analysis sheet | | |
| --- | --- | --- |
| Determination | Specification | Method |
| Fatty acid profile (expressed as FFA) | | |
| EPA (mg/g) | Min 36.5 | Eur. Ph. 2.49.29 |
| DHA (mg/g) | Min 25.0 | Eur. Ph. 2.49.29 |
| DPA (mg/g) | Min 0.45 | Eur. Ph. 2.49.29 |
| Omega-3 total (mg/g) | Min 71.0 | Eur. Ph. 2.49.29 |

TABLE 5-continued

| EMOX-2 technical analysis sheet | | |
| --- | --- | --- |
| Determination | Specification | Method |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| *Escherichia Coli* (CFU/g) | Absent | Eur. Ph. 2.6.13 |
| *Staphylococcus aureus* (CFU/g) | Absent | Eur. Ph. 2.6.13 |
| *Salmonella* spp (CFU/10 g) | Absent | Eur. Ph. 2.6.13 |

Example 3. Industrial Production of an Emulsion with Omega-3 Fatty Acids (Monoglyceride)

In order to carry out the industrial production of 95 kg of an Omega-3 fatty acid emulsion in the form of monoglyceride (MG) in water (EMOX-3), two phases were prepared at room temperature, an aqueous phase and an oily phase, which were subsequently mixed and were emulsified. Table 6 shows the composition of the emulsion.

The aqueous phase was obtained by mixing water, preservatives (potassium sorbate and sodium benzoate) and sweeteners (sucralose and xylitol) under mechanical stirring. In this aqueous phase, the mixture of cellulose derivatives (microcrystalline cellulose and carboxymethyl cellulose), which was activated by means of vigorous stirring, and a hydrophilic emulsifier was also added. The aqueous phase was stirred at room temperature for approximately 10 minutes.

In order to prepare the oily phase, the oil (80/00MAG) was used which is a semi-refined, esterified fish oil concentrated to 80% EPA, transesterified to its monoacetyl glyceride form and lastly deodorized, in addition to containing vitamin E and curcumin as antioxidants. The oil (80/00MAG), which comprises Omega-3 fatty acids in the form of monoglyceride, was mixed with the aromas (lemon aroma and peppermint oil) and the mixture was stirred.

The oily and aqueous phase were mixed and emulsified by means of mechanical stirring for approximately 30 minutes at room temperature. Following emulsification, the mixture was subjected to a pasteurization process for which the emulsified mixture was heated to 75° C. for approximately 7 seconds. After this time, the pH was adjusted with trisodium citrate and the emulsion was preferably cooled at a temperature below 25° C.

TABLE 6

| Composition for 95 kg of EMOX-3 | |
| --- | --- |
| | Composition (% weight) |
| Omega-3 fatty acids | 10 |
| Aroma (lemon oil and peppermint oil) | 1.34 |
| Mixture of celluloses (88% microcrystalline cellulose and 12% carboxymethyl cellulose) | 0.54 |

TABLE 6-continued

Composition for 95 kg of EMOX-3

| | Composition (% weight) |
|---|---|
| Hydrophilic emulsifier | 1.66 |
| Preservatives (0.025% potassium sorbate and 0.025% sodium benzoate) | 0.05 |
| Sweetener (sucralose and xylitol) | 1.76 |
| Antioxidant (curcumin) | 0.006% |
| Trisodium citrate | Depending on the final pH |
| Water | csp 100 |

TABLE 7

Composition of the oil 80/00MAG

| Determination | Specification | Method |
|---|---|---|
| Fatty acid profile (expressed as FFA) | | |
| EPA (mg/g) | Min 800 | Eur. Ph. 2.49.29 |
| Omega-3 total (mg/g) | Min 800 | Eur. Ph. 2.49.29 |
| Contained in MAG (% A) | Min 40 | |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| *Escherichia Coli* (CFU/g) | Absent | Eur. Ph. 2.6.13 |
| *Staphylococcus aureus* (CFU/g) | Absent | Eur. Ph. 2.6.13 |
| *Salmonella* spp (CFU/10 g) | Absent | Eur. Ph. 2.6.13 |
| Antioxidant | | |
| Curcuminoids total (mg/g) | 0.5-0.8 | Internal method |

Example 4. Preparation of an Emulsion, EMOX-4 with Oil (30/20/TG) and Determination of the Particle Size Distribution of the Emulsion In order to carry out the industrial production of 200 gr of an oil emulsion (30/20TG) which comprises Omega-3 fatty acids in the form of triglyceride in water (EMOX-4), two phases were prepared at room temperature, an aqueous phase and an oily phase, which were subsequently mixed and were emulsified. Table 8 shows the composition of the emulsion.

The aqueous phase was obtained by mixing water, preservatives (potassium sorbate and sodium benzoate) and sweeteners (sucralose and xylitol) under mechanical stirring. In this aqueous phase, the mixture of cellulose derivatives (microcrystalline cellulose and carboxymethyl cellulose), which was activated by means of vigorous stirring, and a hydrophilic emulsifier (monoacetyl tartaric and diacetyl tartaric esters of mono and diglycerides of the fatty acids) was also added. The aqueous phase was stirred at room temperature for approximately 10 minutes.

In order to prepare the oily phase, the oil (30/20 TG) was used which is a semi-refined, transesterified and deodorized fish oil which contains vitamin E as an antioxidant. The oil (30/20 TG), which comprises 30% EPA and 20% DHA largely in the form of triglyceride (TG), was mixed with the aromas (pineapple aroma and coconut aroma) and the resulting mixture was stirred.

The oily and aqueous phase were mixed and emulsified by means of mechanical stirring and the pH was adjusted with trisodium citrate. The mixture was maintained under stirring for approximately 30 minutes at room temperature.

TABLE 8

Composition of EMOX-4

| | Composition (% weight) |
|---|---|
| Omega-3 fatty acids | 20 |
| Aroma (pineapple aroma and coconut aroma) | 5 |
| Mixture of celluloses | 0.66 |
| Hydrophilic emulsifier | 2.66 |
| Preservatives (0.02% potassium sorbate and 0.02% sodium benzoate) | 0.04 |
| Sweetener (sucralose and xylitol) | 1.09 |
| Trisodium citrate | Depending on the final pH |
| Water | csp 100 |

Figure 2:
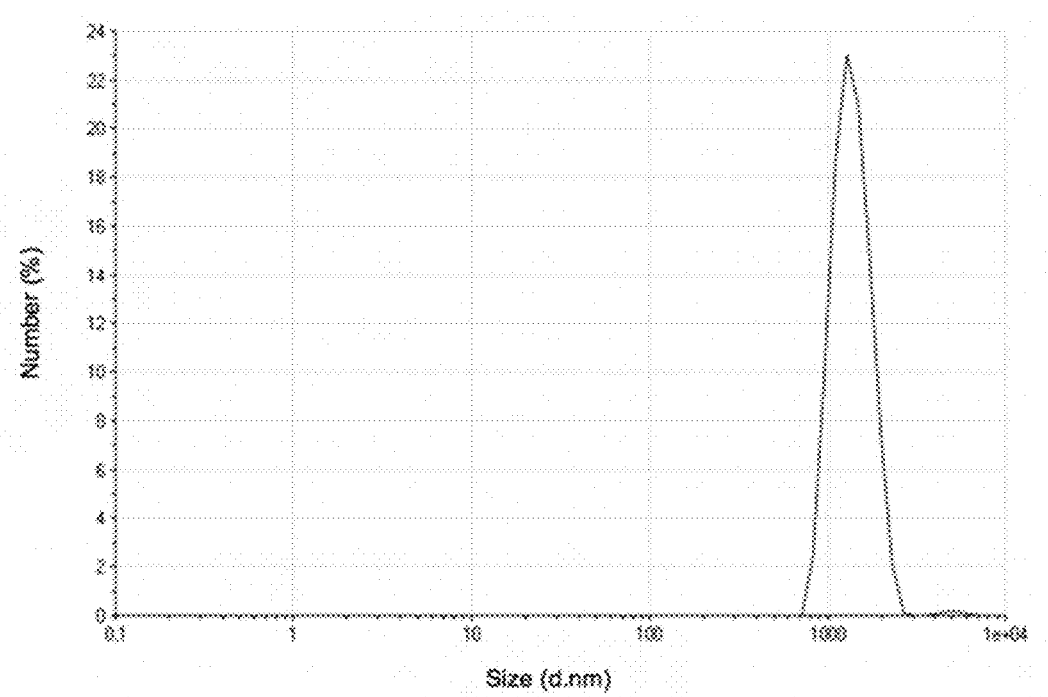
FIG. 2 shows the particle size distribution of the EMOX-2 emulsion, the particle percentage against the particle diameter for an emulsion which contains Omega-3 oil.

This process produced an emulsion (EMOX-4) with a particle size of 1.50 microns as is shown in FIG. 2.

TABLE 9

Composition of the oil 30/20 TG.

| Determination | Specification | Method |
|---|---|---|
| Fatty acid profile (expressed as FFA) | | |
| EPA (mg/g) | Min 278.3 | Eur. Ph. 2.49.29 |
| DHA (mg/g) | Min 182.9 | Eur. Ph. 2.49.29 |
| Triglycerides (% A) | Min 60 | Eur. Ph. 2.49.29 |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| *Escherichia Coli* (CFU/g) | Absent | Eur. Ph. 2.6.13 |
| *Staphylococcus aureus* (CFU/g) | Absent | Eur. Ph. 2.6.13 |
| *Salmonella* spp (CFU/10 g) | Absent | Eur. Ph. 2.6.13 |

Example 5. Preparation of an Emulsion, EMOX-5 with Oil (80/00MAG) and Determination of the Median Particle Size of the Emulsion In order to carry out the industrial production of 100 gr of an emulsion of Omega-3 fatty acids in the form of monoglyceride (monoacetyl glyceride) in water EMOX-5, two phases were prepared at room temperature, an aqueous phase and an oily phase, which were subsequently mixed and were emulsified. Table 10 shows the composition of the emulsion.

The aqueous phase was obtained by mixing water, preservatives (potassium sorbate and sodium benzoate) and sweeteners (sucralose and xylitol) under mechanical stirring. In this aqueous phase, the mixture of cellulose (83.6% microcrystalline cellulose, 11.4% carboxymethyl cellulose and 5% hydroxypropyl methyl cellulose), which was activated by means of vigorous stirring, and a hydrophilic emulsifier was also added. The aqueous phase was stirred at room temperature for approximately 10 minutes.

In order to prepare the oily phase, the oil (80/00MAG) was used which is a semi-refined, esterified fish oil concentrated to 80% EPA, transesterified to its monoacetyl glyceride form and lastly deodorized, in addition to containing vitamin E and curcumin as antioxidants. The oil (80/00MAG) was mixed with the aromas (lemon oil and peppermint aroma) and the mixture was stirred.

The oily and aqueous phase were mixed and emulsified by means of mechanical stirring for approximately 30 minutes at room temperature. The pH was adjusted with trisodium citrate and the emulsion was preferably cooled at a temperature below 25° C.

TABLE 10

Composition per 100 g of EMOX-5

| | Composition (% weight) |
|---|---|
| Omega-3 fatty acids | 10 |
| Aroma (lemon oil and peppermint oil) | 1.53 |
| Mixture of celluloses (83.6% microcrystalline cellulose, 11.4% carboxymethyl cellulose and 5% hydroxypropyl methyl cellulose | 0.80 |
| Hydrophilic emulsifier | 2.33 |
| Preservatives (potassium sorbate and sodium benzoate) | 0.05 |
| Sweetener (sucralose and xylitol) | 1.31 |
| Trisodium citrate | Depending on the final pH |
| Water | csp 100 |

This process produced an emulsion (EMOX-5) with a particle size of 1.25 microns.

TABLE 11

Composition of the oil 80/00MAG used in EMOX-5

| Determination | Specification | Method |
|---|---|---|
| Fatty acid profile (expressed as FFA) | | |
| EPA (mg/g) | Min 800 | Eur. Ph. 2.49.29 |
| Omega-3 total (mg/g) | Min 800 | Eur. Ph. 2.49.29 |
| Contained in MAG (% A) | Min 40 | Eur. Ph. 2.49.29 |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| Escherichia Coli (CFU/g) | Absent | Eur. Ph. 2.6.13 |
| Staphylococcus aureus (CFU/g) | Absent | Eur. Ph. 2.6.13 |
| Salmonella spp (CFU/10 g) | Absent | Eur. Ph. 2.6.13 |

Example 6. Preparation of an Emulsion of Omega-3 Fatty Acids and SPMs (17HDHA and 18HEPE) and Determination of the Particle Size Distribution of the Emulsion and Study of Stability In order to carry out the industrial production of 25 kg of an emulsion of Omega-3 fatty acids and 5% SPMs in EMOX-6 water, two phases were prepared at room temperature, an aqueous phase and an oily phase, which were subsequently mixed and were emulsified. Table 12 shows the composition of the emulsion.

The aqueous phase was obtained by mixing water, preservatives (potassium sorbate and sodium benzoate) and sweeteners (sucralose and ecological cane sugar) under mechanical stirring. In this aqueous phase, the mixture of cellulose derivatives (88% microcrystalline cellulose and 12% xanthan gum), which was activated by means of vigorous stirring, and a hydrophilic emulsifier (monoacetyl tartaric and diacetyl tartaric esters of mono and diglycerides of the fatty acids) was also added. The aqueous phase was stirred at room temperature for approximately 10 minutes.

In order to prepare the oily phase, a semi-refined, esterified, concentrated and deodorized fish oil was used which contains vitamin E as an antioxidants. Said oil, composed of EPA (minimum 150 mg/g, expressed as FFA), DHA (minimum 300 mg/g, expressed as FFA), 17HDHA (minimum 50 mg/g, expressed as FFA) and 18HEPE (minimum 40 ppm, expressed FFA), was mixed. The oil, which comprises the Omega-3 fatty acids and the SPMs (17HDHA and 18HEPE), was mixed with the aromas (lemon oil concentrate and peppermint aroma) and the mixture was stirred.

The oily and aqueous phase were mixed and emulsified by means of mechanical stirring for 30 minutes at room temperature. The pH was adjusted to 6.2 with trisodium citrate and the emulsion was cooled at a temperature below 25° C.

TABLE 12

Composition of EMOX-6

| | Composition (% weight) |
|---|---|
| Omega-3 fatty acids with SPMs | 5 |
| Aromas (lemon oil concentrate and peppermint oil) | 1.2 |
| Mixture of celluloses (88% microcrystalline cellulose and 12% xanthan gum) | 0.67 |
| Hydrophilic emulsifier | 0.33 |
| Preservatives (potassium sorbate and sodium benzoate) | 0.06 |
| Sweetener (sucralose and ecological cane sugar) | 6.72 |
| Trisodium citrate | Depending on the final pH |
| Water | csp 100 |

TABLE 13

Composition of the oil used in EMOX-6

| Determination | Specification | Method |
|---|---|---|
| Fatty acid profile (expressed as FFA) | | |
| EPA (mg/g) | 187.6 | Eur. Ph. 2.49.29 |
| DHA (mg/g) | 342.1 | Eur. Ph. 2.49.29 |
| Total Omega-3 (mg/g) | 629.9 | Eur. Ph. 2.49.29 |
| Content of SPMs | | |
| 17HDHA (mg/kg) | 60.8 | LC/MS |
| 18HEPE (mg/kg) | 87.5 | LC/MS |
| 17HDHA + 18HEPE (mg/kg) | 148.3 | LC/MS |
| Analytical data | | |
| Total aerobic microbial count (CFU/g) | Max $10^4$ | Eur. Ph. 2.6.12 |
| Total count of combination of fungi/molds (CFU/g) | Max $10^2$ | Eur. Ph. 2.6.12 |
| Bile-tolerant gram negative bacteria (CFU/g) | Max $10^2$ | Eur. Ph. 2.6.12 |
| Escherichia Coli (CFU/g) | Absent | Eur. Ph. 2.6.13 |
| Staphylococcus aureus (CFU/g) | Absent | Eur. Ph. 2.6.13 |
| Salmonella spp (CFU/10 g) | Absent | Eur. Ph. 2.6.13 |

Figure 3:
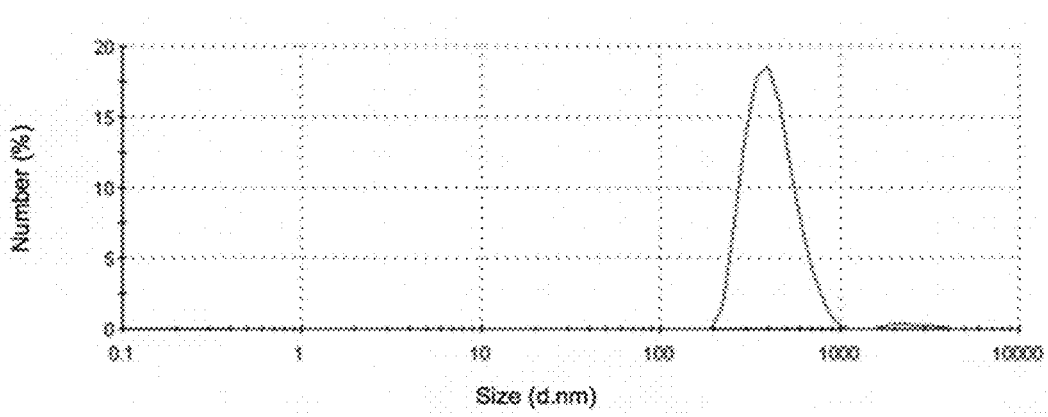
FIG. 3 shows the particle size distribution of the EMOX-3 emulsion, the particle percentage against the particle diameter for an emulsion which contains Omega-3 oil.

This process produced an emulsion (EMOX-6) with a median particle size of 500 nm as is shown in FIG. 3.

Table 14 shows the variation of the properties of the emulsion over time. In order to test the stability of the emulsion, measurements of the median particle size, pH or the coalescence of the particles, amongst others were carried out over time, as is shown in Table 14.

TABLE 14

Study of stability of EMOX-6

| | Time | | | | |
|---|---|---|---|---|---|
| | 0 | 1 month | 2 months | 3 months | 4 months |
| Particle size | 534.6 nm | 555.3 nm | 615.0 nm | 620.3 nm | 650.3 nm |
| pH | 6.71 | 6.68 | 6.70 | 6.73 | 6.70 |
| Centrifugation 300 g - 1 min | Ok | Ok | Ok | Ok | Ok |
| Centrifugation 400 g - 1 min | Ok | Ok | Ok | Ok | Ok |
| Stability under the microscope | Ok | Ok | Ok | Ok | Ok |
| Coalescence constant | $2.0 \times 10^{-8}$ s$^{-1}$ | $2.2 \times 10^{-8}$ s$^{-1}$ | $2.5 \times 10^{-8}$ s$^{-1}$ | $3.0 \times 10^{-8}$ s$^{-1}$ | $3.2 \times 10^{-8}$ s$^{-1}$ |

BIBLIOGRAPHY

Ardalan M R, Rafieian-Kopaei M. Antioxidant supplementation in hypertension. J Renal Inj Prev. 3:39-40. (2014).

Baradaran A. Lipoprotein (a), type 2 diabetes and nephropathy; the mystery continues. J Nephropathol. 1:126-9. (2012).

Birch D G, Birch E E, Hoffman D R, Uauy R D. Retinal development in very-low-birth-weight infants fed diets differing in omega-3 fatty acids. Invest. Ophthalmol. Vis. Sci. 33, 2365-2376. (1992a).

Birch E E, Birch D G, Hoffman D R et al. Dietary essential fatty acid supply and visual acuity development. Invest Ophthalmol Vis Sci. 33:3242-3253. (1992b).

Birch E E, Hoffman D, Uauy R et al. Visual acuity and the essentiality of docosahexaenoic acid and arachidonic acid in the diet of term infants. Pediatric Research. 44:201-209. (1998).

Bourre J, Francois M, Youyou A, Dumont O, Piciotti M, Pascal G et al. The effects of dietary a-linolenic acid on the composition of nerve membranes, enzymatic activity, amplitude of electrophysiological parameters, resistance to poisons and performance of learning tasks in rats. J Nutr. 119:1880-90. (1989).

Cao D, Kevala K, Kim J et al. Docosahexaenoic acid promotes hippocampal neuronal development and synaptic function. J Neurochem. 111:510-521. (2009).

Carlson S. E., Werkman S. H., Rhodes P. G., Tolley E. A. Visual-acuity development in healthy preterm infants: effect of marine-oil supplementation. Am. J. Clin. Nutr. 58, 35-42. (1993).

Cheatham C L, Colombo J, Carlson S E. N-3 fatty acids and cognitive and visual acuity development: Methodological and conceptual considerations. Am J Clin Nutr. 83: 1458S-1466S. (2006).

Cruz-Hernandez C et al., Nutrients, 4, 1781-1793, "Benefits of Structured and Free Monoacylglycerols to deliver eicosapentaenoic (EPA) in a model of lipid malabsorption" (2012).

Dalli, J, Colas R. A. and Serhan C. N. Novel n-3 Immunoresolvents: Structures and Actions. Nature Scientific Reports 3, Article number: 1940. (2013).

Dyall S C. Long-chain omega-3 fatty acids and the brain: a review of the independent and shared effects of EPA, DPA and DHA Frontiers in Aging Neuroscience. 1 April, Volume 7, Article 52. (2015).

Durand G, Antoine J M, Couet C. Blood lipid concentrations of docosahexaenoic and arachidonic acids at birth determine their relative postnatal changes in term infants fed breast milk and formula. Am J Clin Nutr. 70:292-298. (1999).

Garaiova I, Guschina I A, Plummer S F, Tang J, Wang D, Plummer N T. A randomized cross-over trial in healthy adults indicating improved absorption of omega-3 fatty acids by pre-emulsification. Nutrition Journal. 6:4. (2007).

Guisto N M, Salvador G A, Castagnet P I. PAsquare S J, Ilincheta de Bschero M G. Age-associated changes in central nervous system glycerophospholipids composition and metabolism. Neurochem Res. 27:1513-23. (2002).

Hibbeln J R, Davis J M, Steer C, Emmett P, Rogers I, Williams C, et al. Maternal seafood consumption in pregnancy and neurodevelopmental outcomes in childhood (ALSPAC study): an observational cohort study. Lancet. 369:578. (2007).

Hong S, Gronert K, Devchand P R, Moussignac R L, Serhan C N. Novel docosatrienes and 17S-resolvins generated from docosahexaenoic acid in murine brain, human blood, and glial cells. Autacoids in anti-inflammation. J Biol Chem. April 25; 278(17):14677-87. Epub 2003 Feb. 17. (2003).

Ikeda I. Digestion and absorption of structured lipids. In: Chrisyophe A G, DeVriese S, editors. Fat Digestion and Absorption. AOCS Press; Champaign, Ill. pp. 235-243. (2000).

Innis S M. Essential fatty acid metabolism during early development. In: Biology of Metabolism in Growing Animals. Burrin D G ed. Pub. Elsevier Science, B.V. Amsterdam. Part III, pp. 235-74, (2005).

Levy B D, Clish C B, Schmidt B, Gronert K, Serhan C N. Lipid mediator class switching during acute inflammation: signals in resolution. Nat Immunol. July; 2(7):612-9. (2001).

Lewis E J H., Radonic P W, Thomas M. S. Wolever T M S and Wells G D. 21 days of mammalian omega-3 fatty acid supplementation improves aspects of neuromuscular function and performance in male athletes compared to olive oil placebo. Journal of the International Society of Sports Nutrition. 12:28. (2015).

Lindmark L, Clough P. A 5-month open study with long-chain polyunsaturated fatty acids in dyslexia. J Med Food. 10:662-666. (2007).

Mazereeuw G, Lanctot K L, Chau S A, Swardfager W, Herrmann N. Effects of ω-3 fatty acids on cognitive performance: a meta-analysis. Neurobiol Aging. July; 33(7):1482.e17-29. doi: 10.1016/j.neurobiolaging.2011.12.014. Epub 2012 Feb. 3. (2012).

Mirnikjoo B, Brown S E, Kim H F et al. Protein kinase inhibition by ω-3 fatty acids. J Biol Chem. 276(14): 10888-10896. (2001).

Morin C, Fortin S, Cantin A M, Sirois M, Sirois C, Rizcallah E, Rousseau É. Anti-cancer effects of a new docosahexaenoic acid monoacylglyceride in lung adenocarcinoma. Recent Pat anticancer Drug Discov. September 8, (3):319-34. (2013).

Oken E, Wright R O, Kleinman K P, Bellinger D, Amarasiriwardena C J, Hu H, et al. Maternal fish consumption, hair mercury, and infant cognition in a U.S. Cohort. Environ Health Perspect. 113:1376-80. (2005).

Philippoussis F, Przybytkowski E, Fortin S, Arguin C, Pande S V, Steff A-M and Hugo P. Derivatives of monoglycerides as apoptotic agents in T-cells Cell Death Differ. 8:1103-12. (2001).

Rahimi-Madiseh M, Heidarian E, Rafieian-kopaei M. Biochemical components of *Berberis lycium* fruit and its effects on lipid profile in diabetic rats. J HerbMed Pharmacol. 3:15-9. (2014).

Raatz S K, Redmon J B, Wimmergren N, Donadio J V, Bibus D M. Enhanced absorption of omega-3 fatty acids from emulsified compared with encapsulated fish oil. J Am Diet Assoc. June; 109(6): 1076-1081. (2009).

Serhan C N, Hamberg M and Samuelsson B. Lipoxins: Novel series of biologically active compounds formed from arachidonic acid in human leukocytes (lipoxygenase interaction products/conjugated tetraenes/human neutrophils), Proc. Nati. Acad. Sci. USA, Vol. 81, pp. 5335-5339, September (1984).

Serhan C N, Clish C B, Brannon J, Colgan S P, Chiang N, Gronert K. Novel functional sets of lipid-derived mediators with antiinflammatory actions generated from Omega-3 fatty acids via cyclooxygenase 2-nonsteroidal antiinflammatory drugs and transcellular processing. J Exp Med. October 16; 192(8):1197-204. (2000).

Serhan C N, Hong S, Gronert K, Colgan S P, Devchand P R, Mirick G, Moussignac R L. Resolvins: a family of bioactive products of Omega-3 fatty acid transformation circuits initiated by aspirin treatment that counter proinflammation signals. J Exp Med. October 21; 196(8):1025-37. (2002).

Smithers L. G., Gibson R. A., McPhee A., Makrides M. Higher dose of docosahexaenoic acid in the neonatal period improves visual acuity of preterm infants: results of a randomized controlled trial. Am. J. Clin. Nutr. 88, 1049-1056. (2008).

Tavafi M. Diabetic nephropathy and antioxidants. J Nephropathol. 2:20-7. (2013).

Uauy R, Dangour A D. Nutrition in brain development and aging: role of essential fatty acids. Nutr Rev. 64:S24-33. (2006).

Uauy R, Mena P, Rojas C. Essential fatty acids in early life: structural and functional role. Proc Nutr Soc. 59:3-15. (2000).

Yehuda S, Rabinovitz S, Mostofsky D I. Essential fatty acids are mediators of brain biochemistry and cognitive functions. J Neurosci Res. 56:565-570. (1999).

CA 2455226 C, titled "Compositions comprising an o/w emulsion containing conjugated linoleic acid".

CN 103432588 A, titled "Copolymer for preparation of probiotic microcapsule and preparation method thereof".

CN 104274836 A, titled: "Making method for improvement of drug palatability".

CN 100486567 C, titled "Curcumin emulsion and its preparation process".

EP 1116515 A2 titled "Encapsulated liquid".

EP 0868918 B1, titled "Vaccines comprising oil/water emulsion with tocopherol and squalene".

EP 2344140 B1, titled "a method for the production of bioadhesive compact matrices".

EP 2595611 A2, titled "Multiple unit tablet composition".

PCT/CA2008/000530 titled "Compositions comprising polyunsaturated fatty acid monoglycerides or derivatives thereof and uses thereof".

PCT/CA2008/000301 titled "Polyunsaturated fatty acid monoglycerides, derivatives, and uses thereof".

UA99889 C2, titled "Composition Ingredient For Mucoadhesive Polymer".

US 20060029622 A1, titled "Water in oil emulsion comprising sterolesters".

US 20090142324 A1, titled "Oil-in-water type emulsion containing coenzyme q10 and process for producing the same".

US 20090208472 A1, titled "Oil-in-water emulsion composition containing licorice-derived polyphenol".

US 20140170247 A1, titled "Emulsion of Carotenoids and Ocular Antioxidants".

US 201502384 A1, titled "Disintegrating particle composition containing acid-type carboxymethyl cellulose and crystalline cellulose, and orally disintegrating tablet containing said".

U.S. Pat. No. 2,463,738 A, titled "Stable emulsions of oil and glycerine".

U.S. Pat. No. 3,089,823 A, titled "Aqueous vitamin an oil emulsion".

U.S. Pat. No. 5,773,073 A, titled "Water-in-oil emulsion containing a polyglycerol fatty acid ester having erucic acid as the main fatty acid component".

U.S. Pat. No. 6,007,856 A, titled "Oil-in-water dispersions of β-carotene and other carotenoids stable against oxidation prepared from water-dispersible beadlets having high concentrations of carotenoid".

U.S. Pat. No. 8,512,687 B2, titled "Oil in water emulsion comprising NSAIDs and quaternary ammonium halides".

WO99/63841. Titled "Compositions comprising phytosterol and/or phytostanol having enhanced solubility and dispersability".

WO 2003004015 A1, titled "Oil-in-water emulsions comprising a benzodiazepine drug".

WO 2011049629 A2, titled "Methods of making and using compositions comprising flavonoids".

WO 2014051116 A1, titled "Lycopene-containing oil-in-water emulsion composition and production method therefor".

WO 2015102189 A1, titled "Enteric coating composition, enteric coating film and food preparation".

WO 2015104440 A1 titled: "Edible coating for preserving pieces of fruit, production method and application thereof".

The invention claimed is:

1. A composition which is an oil-in-water non-gelled emulsion at room temperature wherein the oil comprises Omega-3 fatty acids wherein the emulsion comprises at least 5% by weight of eicosapentaenoic acid (EPA) and/or docosahexaenoic acid (DHA) with respect to the total weight of the emulsion, and wherein said emulsion also comprises at least two cellulose derivatives which are bonded by means of hydrogen bridges forming a three-dimensional network in which the oil is distributed wherein the cellulose derivatives are selected from microcrystalline cellulose, sodium carboxymethyl cellulose, ethyl hydroxyethyl cellulose, hydroxypropyl methyl cellulose (HPMC), hydroxyethyl methyl cellulose, hydroxypropyl cellulose (HPC), hydroxyethyl cellulose, ethyl methyl cellulose, ethyl cellulose, and/or methyl cellulose, and at least one hydrophilic emulsifier.

2. The emulsion according to claim 1, wherein the total content of cellulose derivatives is less than 5% by weight with respect to the total weight of the emulsion.

3. The emulsion according to claim 1, wherein the emulsion comprises:
   1) 5.0 to 40% by weight of oil which comprises Omega-3 fatty acids;
   2) 0.1 to 5.0% by weight of cellulose derivatives; and
   3) 0.1 to 10% by weight of hydrophilic emulsifier;
   wherein all the percentages by weight are based on the total weight of the emulsion.

4. The emulsion according to claim 1, wherein the oil which comprises the Omega-3 fatty acids is fish oil, krill oil, vegetable oil, microbial oil and/or combinations of these.

5. The emulsion according to claim 1, wherein the emulsion comprises at least 10% by weight of eicosapentaenoic acid (EPA) and/or docosahexaenoic acid (DHA) with respect to the total weight of the emulsion.

6. The emulsion according to claim 1, wherein the emulsion comprises at least 1% by weight of docosapentaenoic acid n-3 (DPA n-3) with respect to the total weight of the emulsion.

7. The emulsion according to claim 1, wherein the Omega-3 fatty acids are in the form of free fatty acids, esters, phospholipids, monoglycerides, diglycerides, triglycerides and/or combinations of these.

8. The emulsion according to claim 1, wherein the Omega-3 fatty acids are in the form of monoglyceride.

9. The emulsion according to claim 1, wherein the Omega-3 fatty acids are in the form of $C_1$-$C_8$ alkyl ester.

10. The emulsion according to claim 1, wherein the oil phase also comprises at least one pro-resolving lipid mediator (SPM).

11. The emulsion according to claim 1, wherein the oil phase also comprises at least one pro-resolving lipid mediator (SPM) selected from lipoxin A4, 15-epi-lipoxin A4, lipoxin B4, 15-epi-lipoxin B4, RvE1, 18S-RvE1, 20-hydroxy-RvE1, RvE2, 18S-RvE2, 18S-RvE3, 18R-RvE3, MaR1, 7S-MaR1, 13R,14S-MaR2, 14S-hydroperoxy-DHA, PDX, 14S,21R-diHDHA, 14R,21S-diHDHA, 14R,21R-diHDHA, 14S,21S-diHDHA, 16,17-diHDHA, 16,17-Epoxy-DHA, 7,8-epoxy-17S-HDHA, PD1, 10S,17S-diHDHA, 16,17S-diHDHA, 16,17-Epoxy-DHA, RvD1, RvD2, RvD3, RvD4, RvD5, RvD6, AT-Rv D1, AT-RvD2, AT-RvD3, AT-RvD4, 10S,17S-HDPAn-6, 17-HDPAn-6, 7,14-diHDPAn-6, 10S,17S-diHDPAn-6, 7,17-diHDPAn-6, 15S-HETE, 15R-HETE, 5S-HEPE, 5R-HEPE, 11S-HEPE, 11R-HEPE, 12S-HEPE, 12R-HEPE, 15S-HEPE, 15R-HEPE, 18S-HEPE, 18R-HEPE, 4S-HDHA, 7S-HDHA, 10S-HDHA, 11S-HDHA, 14S-HDHA, 14R-HDHA, 17S-HDHA, 17R-HDHA, 20S-HDHA, 17S-HDPAn-6, 14S-HDPAn-6, 10S-HDPAn-6, 17S-HDPAn-3, 14S-HDPAn-3, 10S-HDPAn-6, 17-HDPAn-3, 17-hydroperoxy-DPAn-3, RvD1n-3DPA, RvD2 n-3DPA, RvD5 n-3DPA, PD1 n-3DPA, PD2 n-3DPA, 14-HpDHA, MaR1 n-3DPA, MaR2 n-3DPA, MaR3 n-3DPA, and mixtures of the same.

12. The emulsion according to claim 1, wherein the oil phase also comprises at least one pro-resolving lipid mediator selected from 18R/S-HEPE, 17R/S-HDHA, 5S-HEPE, 15RS-HEPE, 4R/S-HDHA, 7R/S-HDHA, 10R/S-HDHA, 14R/S-HDHA and RvE1 and mixtures of the same.

13. The emulsion according to claim 1, wherein the oil phase also comprises between 0.0005% and 1% by weight of a mixture of 17S/R-HDHA and 18S/R-HEPE wherein the percentage by weight is with respect to the total weight of the emulsion.

14. A method for preparing an emulsion as defined in claim 1, which comprises the steps of:
   1) preparing an aqueous phase which comprises at least two cellulose derivatives;
   2) activating the mixture of cellulose derivatives by vigorous stirring of the aqueous phase;
   3) adding at least one hydrophilic emulsifier to the aqueous phase;
   4) preparing an oily phase which comprises the oil that comprises the Omega-3 fatty acids;
   5) mixing the aqueous phase and the oily phase, followed by homogenization.

15. A dietary supplement, nutraceutical product, medical food, pharmaceutical composition, medication, sport nutrition composition, an enteral and/or child nutrition composition which comprises an emulsion as defined in claim 1.

16. A method of treating a disease or disorder which presents an inflammatory component, wherein the method comprises administering to a patient in need of such a treatment a therapeutically effective amount of an emulsion according to claim 1.

17. A method of treating a disease or disorder according to claim 16, wherein the disease or disorder which presents an inflammatory component is selected from Crohn's disease, IBD, fatty liver, wound healing, arterial inflammation, arthritis, psoriasis, urticarial, vasculitis, asthma, ocular inflammation, pulmonary inflammation, dermatitis, cardiovascular diseases, AIDS, Alzheimer's, atherosclerosis, cancer, type 2 diabetes, hypertension, neuromuscular disorders, obesity, infectious diseases, leukemia, lymphoma, metabolic syndrome, obesity, heart attack, rheumatism, transplants, periodontal diseases, brain damage, trauma, cystic fibrosis and muscular disorders.

18. The emulsion according to claim 1, wherein the total content of cellulose derivatives is less than 2% by weight with respect to the total weight of the emulsion.

19. The emulsion according to claim 1, wherein the emulsion comprises at least 15% by weight of eicosapentaenoic acid (EPA) and/or docosahexaenoic acid (DHA) with respect to the total weight of the emulsion.

20. A food or dietary supplement which comprises an emulsion as defined in claim 1.

* * * * *